(12) United States Patent
Cho

(10) Patent No.: US 10,849,646 B2
(45) Date of Patent: Dec. 1, 2020

(54) DEVICE FOR CUTTING ARTIFICIAL ANUS PROTECTION PLATE

(71) Applicant: Jae Young Cho, Seoul (KR)

(72) Inventor: Jae Young Cho, Seoul (KR)

( * ) Notice: Subject to any disclaimer, the term of this patent is extended or adjusted under 35 U.S.C. 154(b) by 123 days.

(21) Appl. No.: 16/069,295

(22) PCT Filed: Jan. 11, 2017

(86) PCT No.: PCT/KR2017/000378
§ 371 (c)(1),
(2) Date: Oct. 26, 2018

(87) PCT Pub. No.: WO2017/123001
PCT Pub. Date: Jul. 20, 2017

(65) Prior Publication Data
US 2019/0046225 A1 Feb. 14, 2019

(30) Foreign Application Priority Data

Jan. 12, 2016 (KR) .................. 10-2016-0003774
Mar. 10, 2016 (KR) .................. 10-2016-0028922
Sep. 28, 2016 (KR) .................. 10-2016-0124869

(51) Int. Cl.
| A61B 17/3205 | (2006.01) |
| A61F 5/445 | (2006.01) |
| B26F 1/38 | (2006.01) |
| A61F 5/44 | (2006.01) |
| B26F 1/32 | (2006.01) |
| A61B 17/32 | (2006.01) |
| A61B 17/3209 | (2006.01) |

(52) U.S. Cl.
CPC .......... *A61B 17/32053* (2013.01); *A61F 5/44* (2013.01); *A61F 5/445* (2013.01); *B26F 1/32* (2013.01); *B26F 1/3846* (2013.01); *A61B 17/32093* (2013.01); *A61B 2017/320052* (2013.01)

(58) Field of Classification Search
CPC .. B26F 1/32; B26F 1/3846; B26F 1/34; B26F 1/386; A61F 5/44; A61F 5/445; A61B 2017/320052; A61B 17/32053; A61B 17/32093; B21D 28/343; B23D 29/02
USPC .... 83/631; 30/360, 277, 367, 301, 316, 358, 30/361
See application file for complete search history.

(56) References Cited

U.S. PATENT DOCUMENTS

| 2,735,489 A | * | 2/1956 | Fowler ................. | B21D 28/343 30/360 |
| 3,255,526 A | * | 6/1966 | Molitor ................. | B21D 28/18 30/360 |
| 3,269,011 A | * | 8/1966 | Herrstrum ............ | B21D 28/343 30/360 |
| 4,380,871 A | * | 4/1983 | Adleman ............... | B23D 29/02 30/360 |

(Continued)

FOREIGN PATENT DOCUMENTS

JP 2000-166952 A 6/2000

*Primary Examiner* — Ghassem Alie
(74) *Attorney, Agent, or Firm* — Rabin & Berdo, P.C.

(57) ABSTRACT

A device for cutting an artificial anus protection plate includes a protection plate support part that supports the artificial anus protection plate, a guide rod screw-coupled to a coupling rod in a lengthwise direction of the coupling rod, and a cutting part that cuts the artificial anus protection plate at a preset diameter.

7 Claims, 21 Drawing Sheets

(56) References Cited

U.S. PATENT DOCUMENTS

| | | | |
|---|---|---|---|
| 4,391,042 A | | 7/1983 | Sunderland |
| 4,403,417 A | * | 9/1983 | Wilson ................. B21D 28/343 30/360 |
| 4,594,779 A | * | 6/1986 | Hagemeyer .......... B21D 28/343 30/360 |
| 4,817,287 A | | 4/1989 | Arnold et al. |
| 4,858,317 A | | 8/1989 | Seib et al. |
| 6,823,764 B1 | | 11/2004 | Tsubota |
| 2012/0023757 A1 | | 2/2012 | Schena |

* cited by examiner

DEVICE FOR CUTTING ARTIFICIAL ANUS PROTECTION PLATE

CROSS-REFERENCE TO RELATED APPLICATIONS

This U.S. non-provisional patent application claims priority under 35 U.S.C. § 119 of Korean Patent Application No. 10-2016-0003774, filed on Jan. 12, 2016, 10-2016-0028922, filed on Mar. 10, 2016, and 10-2016-0124869, filed on Sep. 28, 2016, the entire contents of which are hereby incorporated by reference.

TECHNICAL FIELD

The present invention disclosed herein relates to a device for cutting artificial anus protection plate, and more particularly, to a device for cutting artificial anus protection plate which punches a protection plate to the size of the artificial anus of a user.

BACKGROUND ART

A stoma is a hole, which is formed in the abdomen, when an abnormality in feces or urine occurs, to discharge feces or urine to the outside of the body through a surgery, and functions as an artificial anus.

In the case of a patient who has undergone a stoma surgery for discharging feces and urine, excrements discharged from the stoma formed in the abdomen is collected by using an accommodation means such as a bowel bag and then discarded. For convenience of such stoma patients, various auxiliary stoma apparatuses are used to facilitate the collecting and discarding of the excrements of the stoma patient.

In general, as illustrated in FIGS. 1A and 1B, in the above-mentioned auxiliary stoma apparatuses, a separate fixture for fixing a bowel bag 20 to the skin, that is, an artificial anus protection plate 10, is attached to a stoma, and an auxiliary stoma apparatus such as the bowel bag 20 is coupled to the attached artificial anus protection plate 10.

However, when wearing, for a long time, the above-mentioned skin contact-type auxiliary stoma apparatus, there is a problem in that an excrement leakage may occur, the artificial anus protection plate 10 may be peeled off from the skin, or the skin may be irritated and suffer an injury such as infection or necrosis.

Accordingly, there is a problem in that the artificial anus protection plate 10 attached to the skin should be frequently replaced.

Meanwhile, since the sizes and the formation positions of the stoma vastly vary, a through hole should be cut for the artificial anus protection plate to fit the size and position of the stoma of a patient.

Accordingly, a user should mark the position to be penetrated to the size of an affected area and cut the position by using scissors. However, there are problems in that it is difficult not only for the user to form a through hole with a certain size in the artificial anus protection plate, but also for a user having no skills or inconvenience in hand motions to cut the artificial anus protection plate to the size of the affected area.

DISCLOSURE OF THE INVENTION

Technical Problem

The present invention provides a device for cutting an artificial anus protection plate in which cutting such as boring can be easily and conveniently performed in an artificial anus protection plate by means of a support part for supporting the artificial anus protection plate and a cutting part.

Technical Solution

In accordance with an embodiment of the present invention, disclosed is a device for cutting an artificial anus protection plate, the device including: a protection plate support part in which a coupling rod 110 passing through an artificial anus protection plate 10 and having a male screw section 111 on the outer peripheral surface thereof is installed, and which has a support part 120 for supporting the artificial anus protection plate 10; and a rotary pressing part including a cutting part 210 having a circular blade 211 so as to bore a hole with a preset diameter in the artificial anus protection plate 10, and a pressing body 220 which has a female screw section 222 passing through the cutting part 210 and screw-coupled to the male screw section 111 of the coupling rod 110 and which presses the cutting part 210 toward the support part 120 by means of rotation.

The male screw section 111 may be formed to be spaced apart from an upper end of the coupling rod 110.

The protection plate support part may include a handle part 130 which is coupled to a lower end of the coupling rod 110 and in which a plurality of protruding ribs 131 are formed in a circumferential direction so as to be easily held and rotated by the hand of a user.

The support part 120 has, on an upper surface thereof, a support surface 121 for supporting the artificial anus protection plate 10 and may be detachably coupled to the handle part 130 so as not to be rotatable relative to the handle part 130.

The support part 120 and the handle part 130 may be gear-coupled.

The cutting part 210 may include the circular blade 211 formed of a metal material and a blade coupling part 212 to which the circular blade 211 is fixedly installed and which is detachably coupled to the pressing body 220 so as to disable a rotation relative to the pressing body 220.

The blade coupling part 212 and the pressing body 220 may be coupled to engage with each other by means of a gear structure.

The pressing body 220 may include a hub 221 having: the female screw section 222 formed in an inner peripheral surface thereof; and the blade coupling part 212 inserted into an outer peripheral surface thereof.

The outer peripheral surface of the hub 221 may further have an O-ring 223 installed therein for increasing the contact tightness with the inner peripheral surface of the blade coupling part 212.

The pressing body 220 and the handle part 130 may have the same material and shape.

In accordance with another embodiment of the present invention, disclosed is a device for cutting an artificial anus protection plate, the device including: a protection plate support part in which a coupling rod 110 passing through an artificial anus protection plate 10 and having a male screw section 111 on an outer peripheral surface thereof is installed, and which has a support part 120 for supporting the artificial anus protection plate 10; a pressing body 220 including a coupling part 310 which has a female screw section 222 coupled to the male screw section 111 of the coupling rod 110 by means of rotation, and a pressing part 311 which presses the artificial anus protection plate 10 against the support part 120 when the coupling part 310 is screw-coupled to the male screw section 111 of the coupling rod 110 by means of rotation; and a cutting part 210 which rotatably passes through the coupling part 310 and has a circular blade 211 so that a hole is bored in the artificial anus protection plate 10 at a preset diameter, wherein the artificial anus protection plate 10 is fixed to the support part 120 by means of pressing of the pressing part 311 and then the cutting part 210 is rotated to bore a hole in the artificial anus protection plate 10.

The pressing body 220 may include a guide coupling rod 320 to which the coupling part 310 is screw-coupled and which is screw-coupled to the pressing body 220, and the pressing part 311 may be formed on an end of the coupling part 310.

The protection plate support part may include a handle part 130 coupled to a lower end of the coupling rod 110, the pressing body 220 may have a body shape formed corresponding to the handle part 130 of the protection plate support part, and the cutting part 210 may have a body shape formed corresponding to the handle part 130 of the protection plate support part so as to be rotated by a user.

The pressing body 220 may include a guide coupling rod 320 to which the coupling part 310 is screw-coupled and which is screw-coupled to the pressing body 220, the pressing part 311 may be formed to protrude in the lengthwise direction from the pressing body 220 so that the cutting part 210 is located inside the pressing part, and the pressing part 311 may have one or more openings 225 so that a user may rotate the cutting part 210.

An elastic member 400 may be installed between the cutting part 210 and the pressing body 220 so that the cutting part 210 is pressed toward the support part 120.

In accordance with another embodiment of the present invention, disclosed is a device for cutting an artificial anus protection plate, the device including: a protection plate support part 130 in which a coupling rod 110 passing through an artificial anus protection plate 10 is installed and a support surface 135 for supporting the artificial anus protection plate 10 is formed; a guide rod 500 screw-coupled to the coupling rod 110 in the lengthwise direction of the coupling rod 110; a cutting part 210 installed so as to be movable in the vertical direction with respect to the guide rod 500 and having a blade section 212 for cutting the artificial anus protection plate 10 at a preset diameter; and a pressing means which is coupled to the guide rod 500 and presses to move the cutting part 210 downward so that the blade section 212 cuts the artificial anus protection plate 10.

The pressing means may include: a cylinder part 610 to which an upper end of the guide rod 500 is inserted and coupled; a pressing part 630 which is coupled to a lower side of the cylinder part 610 so as to be movable in the vertical direction with respect to the cylinder part 610 and forms a second cylinder space S2 with the cylinder part 610 and which presses the cutting part 210 by means of a pressure inside the second cylinder space S2; and a pressing body part 620 which is coupled to an upper side of the cylinder part 610 so as to be movable in the vertical direction with respect to the cylinder part 610, forms with the cylinder part 610 a first cylinder space S1 communicating with the second cylinder space S2, and includes a piston member 623 moving downward along the first cylinder space S1 such that a pressure in the first cylinder space S1 is transferred to the second cylinder space S2.

The pressing part 630 may include a cylinder member 610 which is installed so as to be movable in the vertical direction while being in close contact with an inner peripheral surface of the cylinder space section formed in a bottom surface of the cylinder part 610.

The pressing part 630 may include a cylinder member 610 in which a cylinder space section is formed in an upper portion thereof so that an outer peripheral surface of the cylinder part 610 is inserted in the cylinder space section and is movable in the vertical direction.

The pressing part 630 may be formed as a separate member from the cutting part 210 or integrally formed with the cutting part 210.

The pressing body part 620 may have a rotation prevention means installed therein to prevent rotation about the guide rod 500 as a rotation axis.

The rotation prevention means may include: one or more rotation prevention grooves 611 formed in the outer peripheral surface of the cylinder part 610 in the vertical direction; and engagement protrusions 621 protruding toward the inner peripheral surface of the pressing body part 620 and inserted into the rotation prevention grooves 611.

The cutting part 210 may include: a blade section 212 formed of a metal material; and a blade coupling section 211 to which the blade section 212 is fixedly installed.

A lower end of the blade section 212 may have any one shape among rectangles, circles, ellipses, polygons, and freely curved shapes.

Advantageous Effects

A device for cutting an artificial anus protection plate in accordance with an embodiment of the present invention has a merit in that a through hole can be easily formed in the artificial anus protection plate by combining a support part for supporting the artificial anus protection plate and a cutting part provided with a circular blade having a preset diameter.

In addition, a device for cutting an artificial anus protection plate in accordance with an embodiment of the present invention has a merit in that the circular blade is detachably coupled to a rotary pressing part and circular blades with different diameters can thereby be selectively coupled, so that through holes with various sizes may be conveniently cut.

In addition, a device for cutting an artificial anus protection plate in accordance with an embodiment of the present invention has a merit in that the cutting part is detachable coupled such that the cutting parts having blades with different shapes and sizes are selectively coupled, and thus, through holes etc. can be conveniently cut by means of more various methods.

In addition, a device for cutting an artificial anus protection plate in accordance with an embodiment of the present invention has a merit in that each of constituent members is easily attached and detached, so that the device is convenient for carry and maintenance.

In addition, a device for cutting an artificial anus protection plate in accordance with an embodiment of the present invention has a merit in that the main components of the support part and the rotary pressing part have the same shapes and can thereby be injection-molded by means of a single mold, and thus, manufacturing costs can be reduced.

In addition, a device for cutting an artificial anus protection plate in accordance with an embodiment of the present invention has a merit in that the artificial anus protection plate is fixed with the support part and then the circular blade is rotated, so that the boring of the artificial anus protection plate is more convenient.

MODE FOR CARRYING OUT THE INVENTION

Figure 1A:
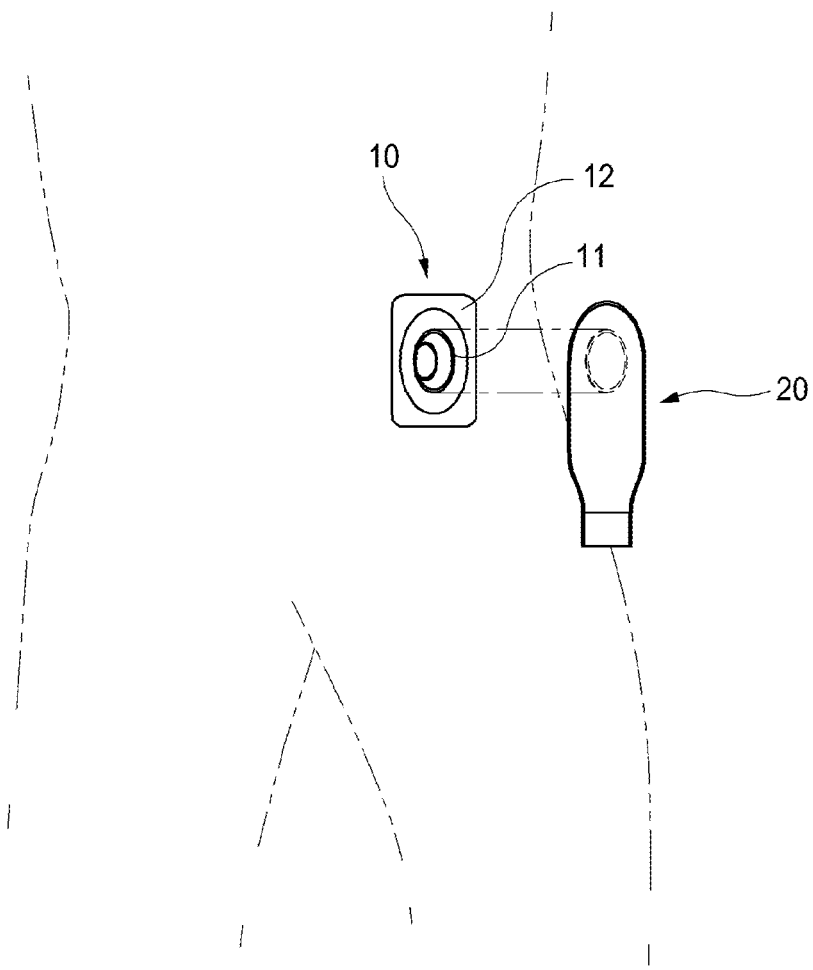
FIG. 1A is a perspective view illustrating an installation example of an artificial anus bag and a protection plate which are conventionally used.

Hereinafter, a device for cutting an artificial anus protection plate in accordance with the present invention will be described in conjunction with the accompanying drawings.

As illustrated in FIGS. 2 to 5, a device for cutting an artificial anus protection plate includes: a protection plate support part in which a coupling rod 110 penetrating an artificial anus protection plate 10 and having a male screw section 111 formed on the outer peripheral surface thereof is installed and which has a support part 12 for supporting the artificial anus protection plate 10; and a rotary pressing part including a cutting part 210, which has a circular blade 211 for boring a hole in the artificial anus protection plate 10 at a preset diameter, and a pressing body 220, which has a female screw section 222 passing through the cutting part 210 and screw-coupled to the male screw section 111 of the coupling rod 110, and which presses the cutting part 210 toward the support part 120 by means of rotation.

The artificial anus protection plate 10 is a component attached to the skin of a user so as to be couplable to a bowel bag 20 and may be variously configured.

Figure 1B:
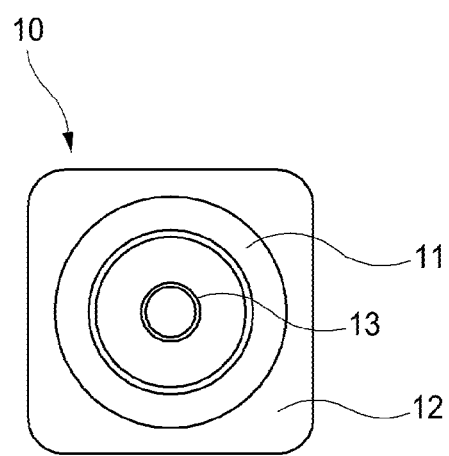
FIG. 1B is a plan view illustrating the protection plate of FIG. 1A.

For example, as illustrated in FIGS. 1A and 1B, the artificial anus protection plate 10 may include: a fixture 11 in which an opening section is detachably formed; and an attachment part 12 which is formed so that the bowel bag 20-attached fixture 11 may be tightly attached to the skin of a user.

At this point, in the central portion of the artificial anus protection plate 10, a cutting hole 13 may be formed so that the user may easily bore a hole at a position to cut.

Meanwhile, the device for cutting an artificial anus protection plate is characterized in that a through hole is formed in the artificial anus protection plate 10 to fit the size of the stoma of the user with respect to the cutting hole 13, and characterized by including a protection plate support part and a rotary pressing part.

The protection plate support part is a component in which a coupling rod 110 passing through the artificial anus protection plate 10 and having a male screw section 111 formed on the outer peripheral surface thereof is installed, and which has a support part 120 for supporting the artificial anus protection plate 10, and may be variously configured.

Specifically, the protection plate support part is a component which supports the artificial anus protection plate 10 so that the artificial anus protection plate 10 may be cut when coupled, by means of rotation, to the rotary pressing part to be described later, and may be variously configured.

For example, the protection plate support part may include: a support part 120 by which the artificial anus protection plate 10 is supported; and a coupling rod 110 which has one end coupled to the support part 120 and the other end inserted into a cutting hole 13 of the artificial anus protection plate 10 to fix the artificial anus protection plate 10.

The coupling rod 110 is a component which has the male screw section 111 on the outer peripheral surface thereof so that the coupling rod 110 is inserted into the artificial anus protection plate 10 and then may be screw-coupled to the rotary pressing part to be described later, particularly, to the female screw section 222 of the pressing body 220 to be described later. The coupling rod may be variously coupled.

At this point, the male screw section 111 is preferably formed on at least a portion of the outer peripheral surface while being spaced apart from the upper end of the coupling rod 110.

As described above, when the male screw section 111 is formed on at least a portion of the outer peripheral surface of the coupling rod 110 while being spaced apart from the upper end of the coupling rod 110, a portion of the upper end portion on which the male screw section 111 is not formed is inserted and is then screw-coupled to the female screw section 222 of the pressing body 220, so that the moving distance of the pressing body 220 in the lengthwise direction of the coupling rod 110 is reduced and the cutting time of the artificial anus protection plate 10 can thereby be reduced.

The male screw section 111 may have any structure as long as the structure can be screw-coupled to the female screw section 222 of the pressing body 220 to be described later.

Meanwhile, a handle part 130 for rotation when the coupling rod 110 is screw-coupled to the female section 222 of the pressing body 220 is installed on a lower end portion of the coupling rod 110.

The handle part 130 is a component which is coupled to the lower end portion of the coupling rod 110 and allows a user to easily hold and rotate the handle part 130.

Figure 2:
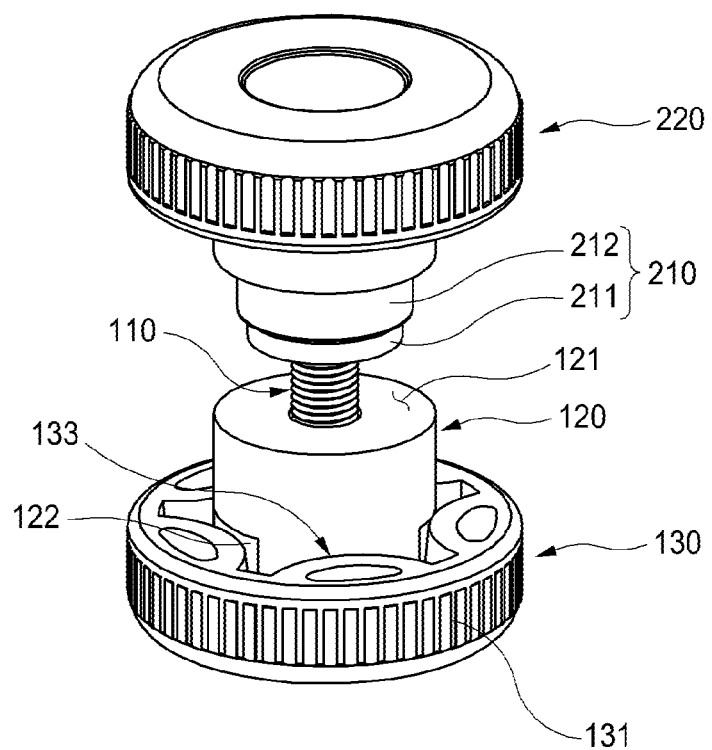
FIG. 2 is a perspective view illustrating an embodiment of a device for cutting an artificial anus protection plate in accordance with the present invention.
Figure 3:
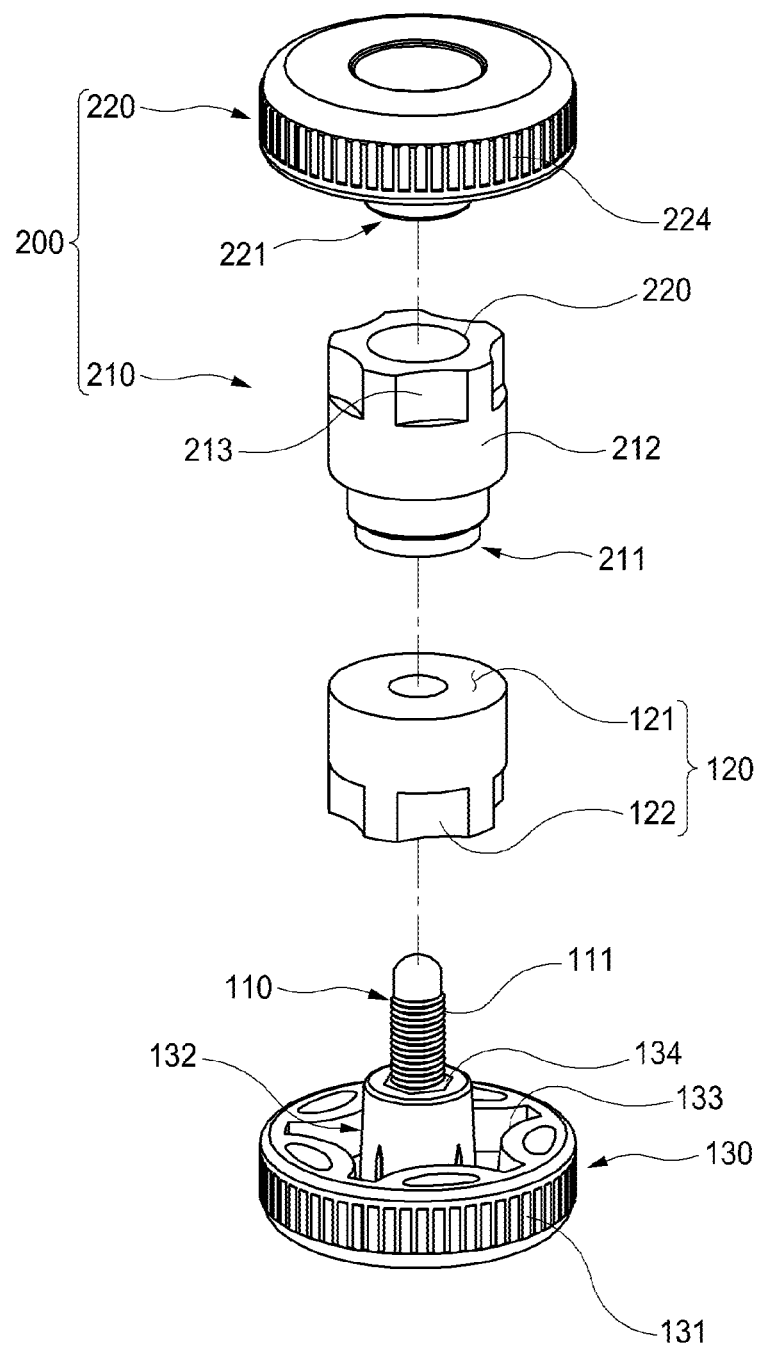
FIG. 3 is an exploded perspective view illustrating a configuration of the device for cutting an artificial anus protection plate of FIG. 2.
Figure 4A:
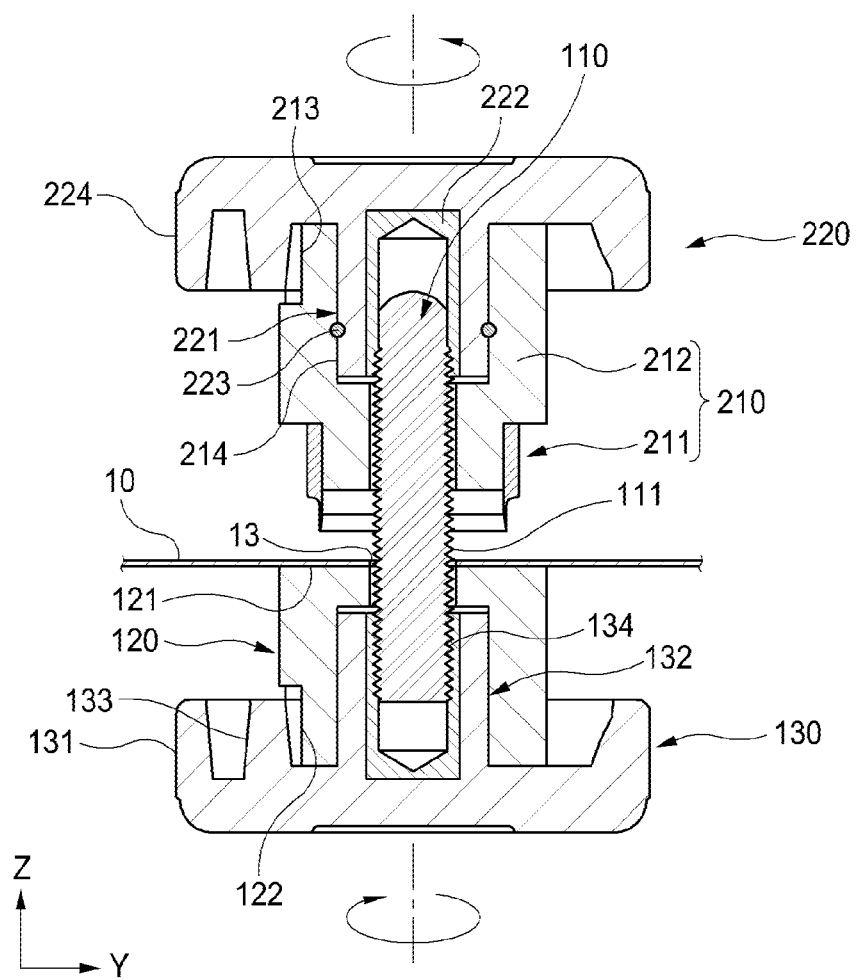
FIGS. 4A and 4B are cross-sectional views illustrating use examples of the device for cutting an artificial anus protection plate of FIG. 2.
Figure 4B:
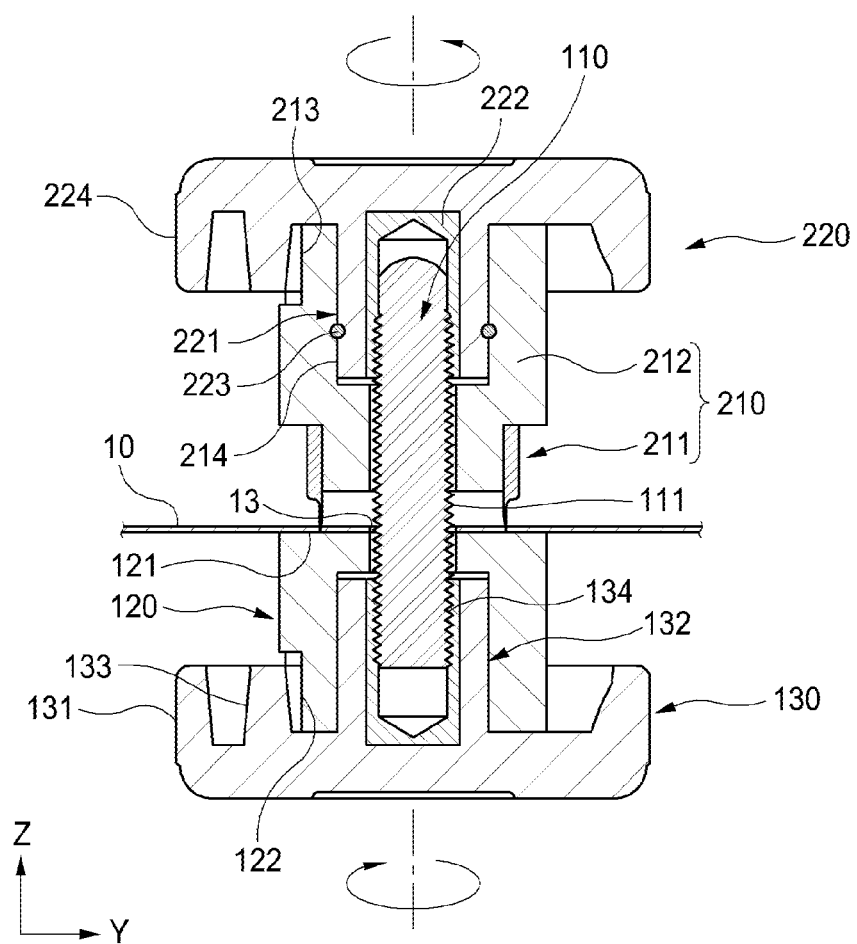

For example, as illustrated in FIGS. 2 and 3, the handle part 130 may include: a fixed hub 134 to which the coupling rod 110 is fixedly installed; and a handle coupling section 132 on which the fixed hub 134 is installed and into which the support part 120 to be described later is detachably inserted.

At this point, the handle part 130 and the support part 120 may be coupled by means of gear structures engaging with other and prevent unnecessary rotation of the support part 120 when the coupling rod 110 rotates.

In addition, on the inner peripheral surface of the handle part 130, one or more second rotation prevention sections 133 may be installed and coupled to a first rotation prevention section 122 formed on the support part 120 to be described later by means of gear structures engaging with each other.

In addition, the second rotation prevention section 133 may be integrally formed with the handle part 130.

Meanwhile, on the outer peripheral surface of the handle part 130, a sliding prevention means for preventing the sliding of the handle part 130 from the hand of a user during rotation may further be provided.

For example, the sliding prevention means may be formed by a plurality of protruding ribs 131 formed on the outer peripheral surface of the handle part 130 in the circumferential direction.

The plurality of ribs 131 are components formed to allow a user to easily hold the ribs by the hand, and may have various shapes as long as the shapes are formed to allow the user to easily hold by the hand.

The support part 120 is a component for supporting the artificial anus protection plate 10 and may be variously configured.

Specifically, the support part 120 is a component which supports the artificial anus protection plate 10 so that the artificial anus protection plate 10 is bored by a circular blade 211 to be described later when the coupling rod 110 and the pressing body 220 are screw-coupled, and may be variously configured, for example, to have a circular supporting surface 121.

For example, as illustrated in FIGS. 2 and 3, the support part 120 may include: a supporting surface 121 formed on an upper portion thereof; and a first rotation prevention section 122 formed on a lower portion of the support part 120 so as to disable a rotation relative to the handle part 130.

At this point, the supporting surface 121 is formed of an elastic material and allows the circular blade 211 to be described later to easily bore a hole in the artificial anus protection plate 10 when the coupling rod 110 and the pressing body 220 are screw-coupled.

In addition, the first rotation prevention section 122 is a component formed on a lower portion of the support part 120 to disable a rotation thereof relative to the handle part 130, and may be variously configured.

The rotary pressing part is a component for boring a through hole with a preset diameter in the artificial anus protection plate 10, and may be variously configured.

For example, the rotary pressing part may include: a cutting part 210 for boring a through hole with a preset diameter in the artificial anus protection plate 10; and a pressing body 220 which presses the cutting part 210.

The cutting part 210 is a component for boring a through hole with a preset diameter in the artificial anus protection plate 10, and may be variously configured.

For example, the cutting part 210 may include: a circular blade 211 formed of a metal material; and a blade coupling part 212 detachably coupled to the pressing body 220 so as to disable a rotation thereof relative to the pressing body 220.

In addition, the circular blade 211 may have a different structure coupled to the blade coupling part 212 according to the diameter thereof.

Figure 5:
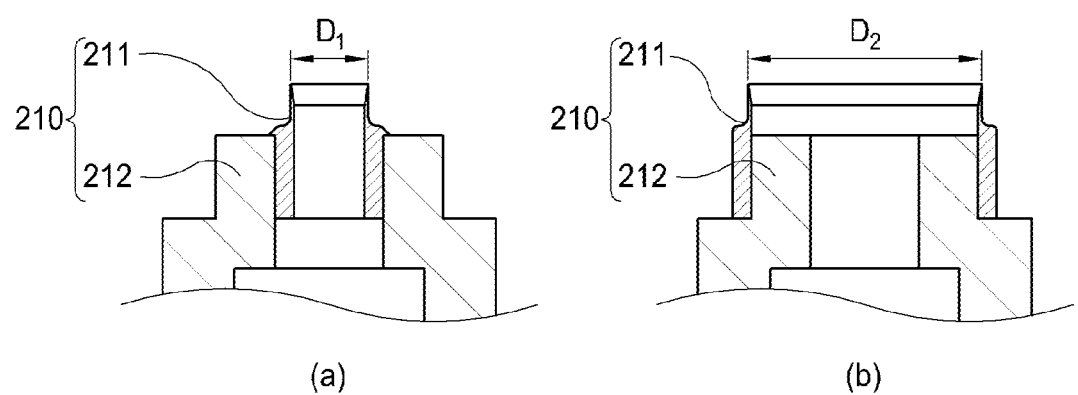
FIG. 5 is a partial perspective view illustrating a modified example of the cutting part installed in FIG. 2.
Figure 6:
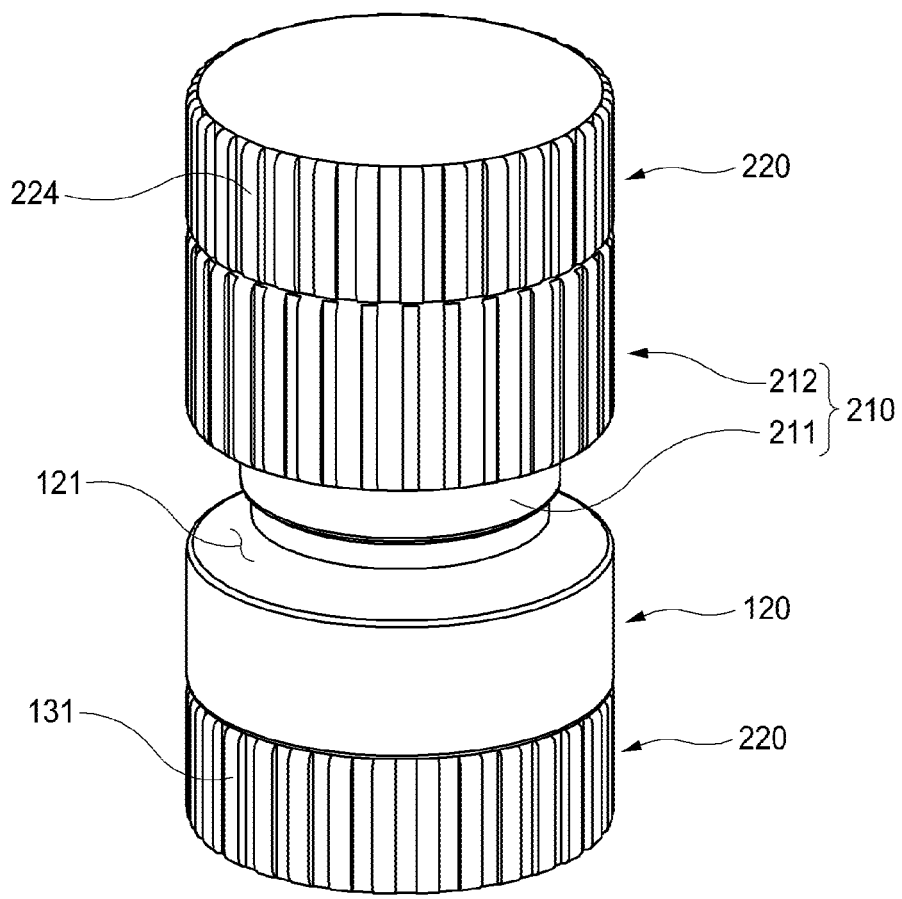
FIG. 6 is a perspective view illustrating a second embodiment of a device for cutting an artificial anus protection plate in accordance with the present invention.

For example, the circular blade 211, as illustrated in a of FIG. 5, may be inserted into the blade coupling part 212 when the diameter D1 is relatively small.

In another example, the circular blade 211, as illustrated in b of FIG. 5, may be coupled such that the outer peripheral surface of the blade coupling part 212 is inserted when the diameter D2 is relatively large.

In addition, the circular blade 211 may have one or more rotation prevention protrusions not shown which are further provided on a coupling position at which the circular blade is coupled to the blade coupling part 212 so as to disable a rotation relative to the pressing body 220.

Here, the circular blade 211 is rotated together with the pressing body 220 when the pressing body 220 is rotated relative to the protection plate support part, so that a through hole may be smoothly formed in the artificial anus protection plate 10.

Specifically, the circular blade 211 is rotated together relative to the artificial anus protection plate 10 supported by the protection plate support part, and hence smoothly cuts the portion corresponding to the through hole in the artificial anus protection plate 10.

Meanwhile, the pressing body 220 is a component for pressing the cutting part 210 toward the support part 120 by means of rotation, and may be variously configured.

In addition, the pressing body 220 may have the same material and shape as the handle part 130.

For example, the pressing body 220 may include a hub 221 in which the female screw section 222 is formed in the inner peripheral surface thereof and blade coupling part 212 is inserted into the outer peripheral surface thereof.

The female screw section 222 has a structure formed to pass through the cutting part 210 and be screw-couplable to the male screw section 111 of the coupling rod 110, and may have various structures.

In addition, the hub 221 may have various structures as long as the structures can be inserted and installed in an inner peripheral surface 213 of the blade coupling part 212.

Here, on the outer peripheral surface of the hub section 221, an O-ring 223 may further be installed to increase the attachment strength to the inner peripheral surface 213 of the blade coupling part 212.

In addition, on the outer peripheral surface of the pressing body 220, a sliding prevention means for preventing the sliding of the pressing body 220 from the hand of a user during rotation of the pressing body 220 may further be provided.

For example, the sliding prevention means may be a plurality of protruding ribs 224 on the outer peripheral surface of the pressing body 220 in the circumferential direction.

Meanwhile, as illustrated in FIGS. 1 to 5, a device for cutting an artificial anus protection plate is characterized in that some components of a support part and some components of a rotary pressing part can be formed in shapes symmetrical to each other.

In particular, when some components of a support part and some components of a rotary pressing part can be formed in shapes symmetrical to each other, a synthetic resin is used as the material of each of constituent members, and the number of molds used during manufacturing is reduced, and thus, the total production costs and the replacement costs when partial damage occurs may be saved.

Meanwhile, the device for cutting an artificial anus protection plate having the above-mentioned configuration has a merit in that there is provided the female screw section 222 which passes through the cutting part 210 and is screw-coupled to the male screw section 111 of the coupling rod 110, and the cutting part 210 is pressed toward the support part 120 by means of rotation, and thus, a through hole may be conveniently formed in the artificial anus protection plate 10.

However, there may be a problem in that when boring a hole by means of the cutting part 210 by using the screw-coupling between the coupling rod 110 and the pressing body 220 for pressing the cutting part 210 toward the support part 120 by means of rotation, a portion of the artificial anus protection plate 10 is not cut.

Specifically, due to a positional deviation of the pitches of the screws facing each other with respect to a central axis when the coupling rod 110 and the pressing body 220 are screw-coupled, there may be a problem in that a portion of the artificial anus protection plate 10 is not cut when boring a hole by means of the cutting part 210.

Accordingly, a user presses the cutting part toward the support part 120 by means of sufficient force and rotation, thereby forming a through hole in the artificial anus protection plate 10.

Meanwhile, in second and third embodiments of the present invention, such a problem may be resolved when only a cutting part 210 is idly rotated in a state in which an artificial anus protection plate 10 is pressed toward a support part 120 and fixed, and a hole is thereby bored in the artificial anus protection plate 10.

Specifically, as illustrated in FIGS. 6 to 11B, in accordance with another embodiment of the present invention, a device for cutting an artificial anus protection plate includes: a protection plate support part having a support part 120 in which a coupling rod 110 passing through an artificial anus protection plate 10 and having a male screw section 111 on an outer peripheral surface thereof and which supports the artificial anus protection plate 10; a pressing body 220 including a coupling part 310 which has a female screw section 222 coupled, by means of rotation, to the male screw section 310 of the coupling rod 110, and a pressing part 311 which presses the artificial anus protection plate 10 against the support part 120 when the coupling part 310 is screw-coupled, by means of rotation, to the male screw section 111 of the coupling rod 110; and a cutting part 210 which rotatably passes through the coupling part 310 and has a circular blade 211 so that a hole is bored in the artificial anus protection plate 10 at a preset diameter, wherein the artificial anus protection plate 10 is fixed to the support part 120 by means of pressing of the pressing part 311 and then the cutting part 210 is rotated to bore a hole in the artificial anus protection plate 10.

The protection plate support part is a component which supports the artificial anus protection plate 10 so that the artificial anus protection plate 10 may be fixed when coupled, by means of rotation, to the pressing body 220 to be described later, and may be variously configured.

For example, the protection plate support part may have: a coupling rod 110 installed therein, passing through the artificial anus protection plate 10, and having a male screw section 111 formed on the outer peripheral surface thereof, and a support part 120 for supporting the artificial anus protection plate 10.

The support part 120 is a component for supporting the artificial anus protection plate 10 and may be variously configured.

For example, the support part 120 may have a circular support surface 121 which fixes the artificial anus protection plate 10 with a pressing part 311 to be described later by means of rotation of the pressing body 220 and supports the artificial anus protection plate 10 so that a hole is bored by means of a circular blade 211 in the artificial anus protection plate 10.

In addition, the support surface 121 may further have a protrusion 124 protruding upward around the coupling rod 110 in the vicinity of the coupling rod.

The protrusion 124 pushes upward a portion of the artificial anus protection plate 10 in the vicinity of the coupling rod 110 when the coupling rod 110 is inserted into a cutting hole 13 of the artificial anus protection plate 10, so that the pressing part 311 to be described later may more effectively press the artificial anus protection plate 10 against the support part 120.

The coupling rod 110 is a component which has the male screw section 111 on the outer peripheral surface thereof so that the coupling rod 110 may be inserted into the artificial anus protection plate 10 and then be screw-coupled to the pressing body 220 to be described later, particularly, to the female screw section 222 of the pressing body 220. The coupling rod may be variously coupled.

The male screw section 111 may have any structure as long as the structure can be screw-coupled to the female screw section 222 of the pressing body 220 to be described later.

Meanwhile, a handle part 130 for rotation when the coupling rod 110 is screw-coupled to the female section 222 of the pressing body 220 may be installed on a lower end portion of the coupling rod 110.

Specifically, on the outer peripheral surface of the handle part 130, a sliding prevention means for preventing the sliding of the handle part 130 from the hand of a user during the rotation of the handle part 130 may further be provided.

For example, the sliding prevention means may be formed by a plurality of protruding ribs 131 formed on the outer peripheral surface of the handle part 130 in the circumferential direction.

The plurality of ribs 131 are components formed to allow a user to easily hold the ribs by the hand, and may have various shapes as long as the shapes are formed to allow the user to easily hold by the hand.

Meanwhile, the plurality of ribs 131 may be formed not only on the handle part 130 coupled to the lower end portion of the coupling rod 110, but also on the outer peripheral surfaces of the pressing body 220 and the cutting part 210 which will be described later.

The pressing body 220 is a component which is coupled to the coupling rod 110 and presses the artificial anus protection plate 10 against the support part 120, and may include: a coupling part 310 having a female screw section 222 screw-coupled, by means of rotation, to the male screw section 111 of the coupling rod 110; and a pressing part 311 which presses the artificial anus protection plate 10 against the support part 120 when the coupling part 310 is screw-coupled, by means of rotation, to the male screw section 111 of the coupling rod 110.

Through the above-mentioned configuration, the pressing body 220 presses the artificial anus protection plate 10 so that the artificial anus protection plate 10 is fixed to the support part 120 in the inside or outside of the circular blade 211 according to the diameter of the circular blade 211 coupled to the cutting part 210.

Meanwhile, the pressing body 220 preferably has a body shape corresponding to the handle part 130 of the protection plate support part.

In particular, the body of the pressing body 220 may have the same shape and structure as the handle part 130 of the protection plate support part in order to use the same mold during injection molding.

In addition, the coupling part 310 is a component having the female screw section 222 screw-coupled to the male screw section 111 of the coupling rod 110 by means of rotation, and may be variously configured.

In particular, the coupling part 310 may be variously configured, for example, integrally formed with a lower end of the body of the pressing body 220 or formed as a separate member.

Figure 7:
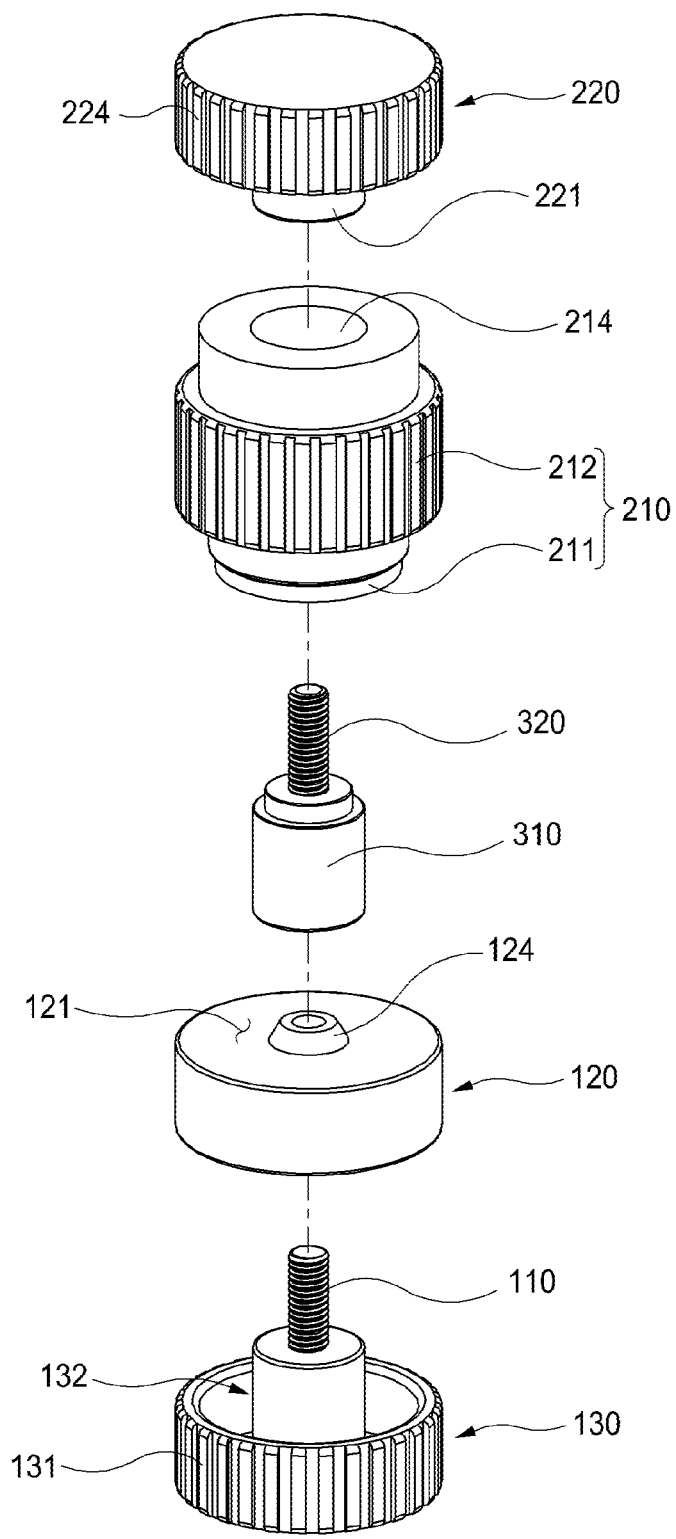
FIG. 7 is an exploded perspective view illustrating a configuration of the device for cutting an artificial anus protection plate of FIG. 6.

Preferably, as illustrated in FIG. 7, the body of the pressing body 220 has the same shape and structure as the handle part 130 of the protection plate support part. Accordingly, the coupling part is formed as a separate member so as to be coupled to the lower end of the body of the pressing body 220, and at this point, may include a guide coupling rod 320, both ends of which are screw-coupled to the coupling part 310 and the body of the pressing body 220.

The guide coupling rod 320 has a structure which is installed so that the structure may be screw-coupled to the coupling part 310 and the pressing body 220, and may have various structures.

Figure 8A:
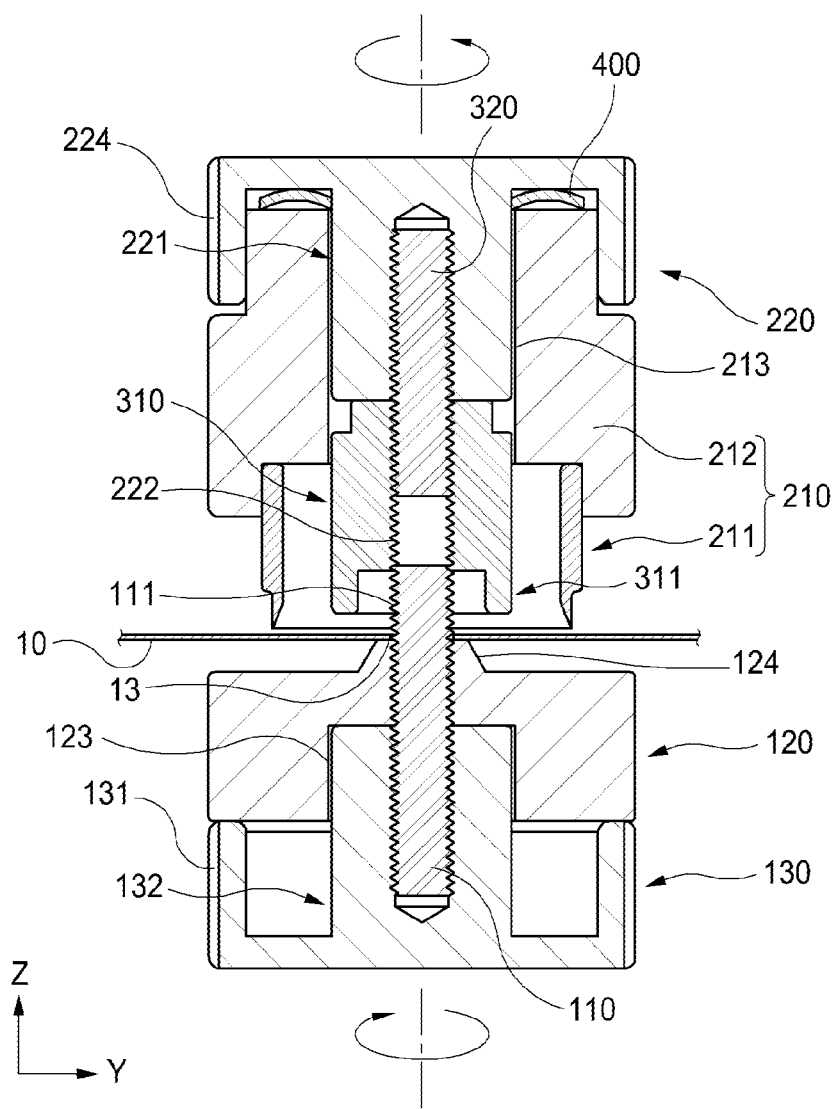
FIGS. 8A and 8B are cross-sectional views illustrating use examples of the device for cutting an artificial anus protection plate of FIG. 6.
Figure 8B:
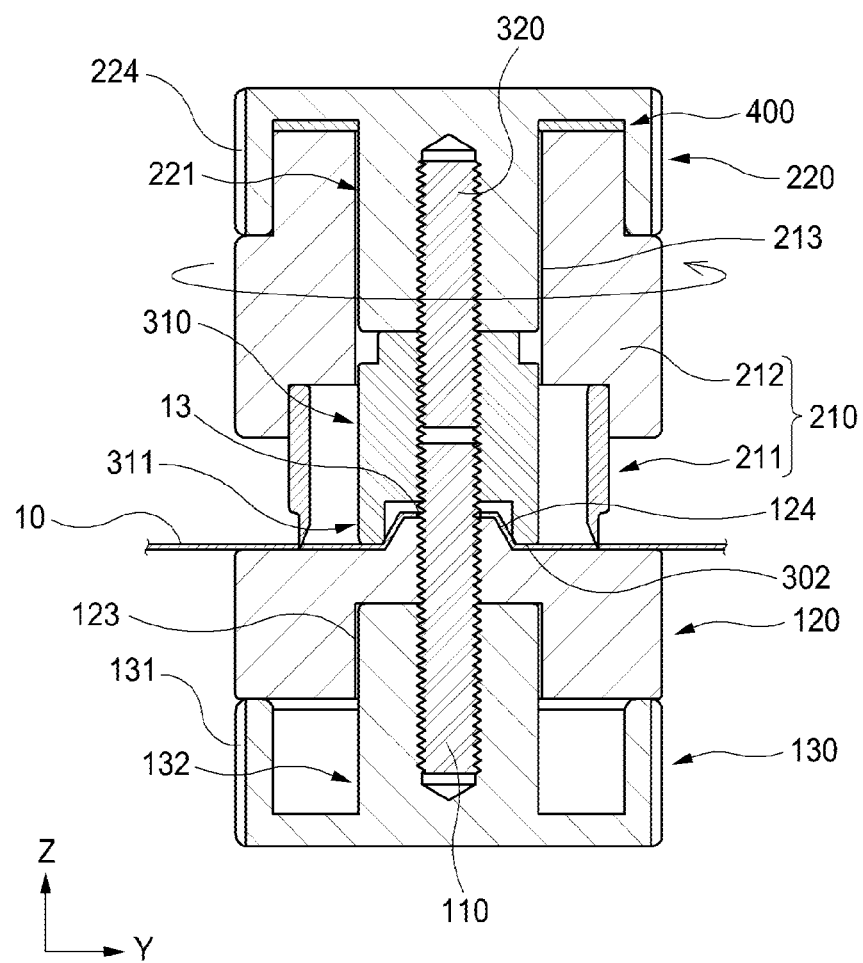
Figure 9:
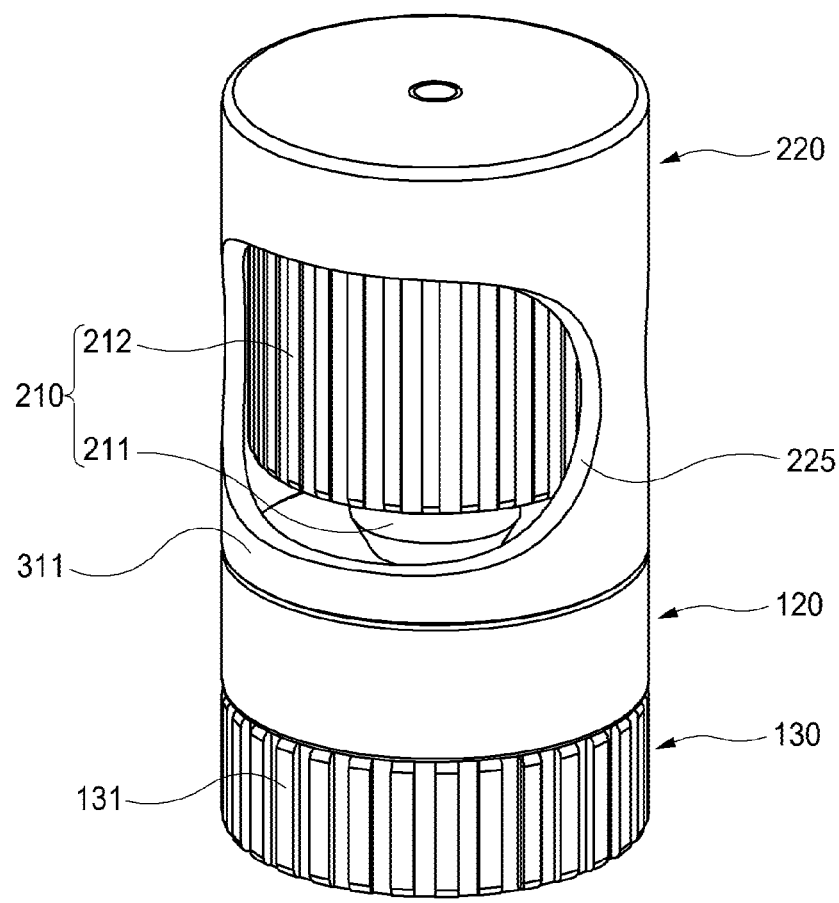
FIG. 9 is a perspective view illustrating a third embodiment of a device for cutting an artificial anus protection plate in accordance with the present invention.
Figure 10:
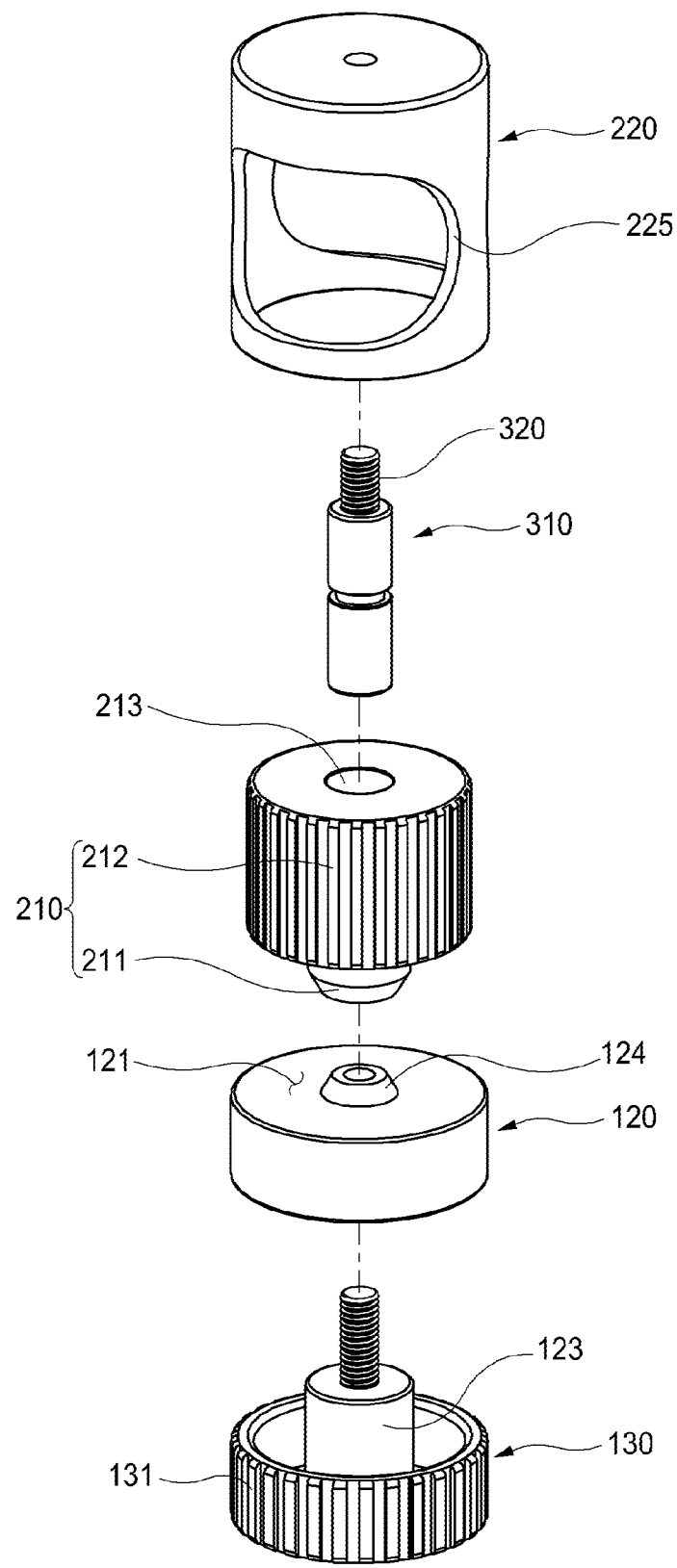
FIG. 10 is an exploded perspective view illustrating a configuration of the device for cutting an artificial anus protection plate of FIG. 9.

Here, as illustrated in FIGS. 7 to 8B, the guide coupling rod 320 may be screw-coupled to the coupling part 310 or as illustrated in FIGS. 9 to 11B, may be integrally formed with the coupling part 310.

In addition, the guide coupling rod 320 may, of course, be integrally formed with the body of the pressing body 220.

The pressing part 311 has a structure formed so that the structure may press the artificial anus protection plate 10 against the support part 120, and may have various structures.

For example, as illustrated in FIGS. 8A and 8B, the pressing part 311 may protrude from an end of the coupling part 310 around the female screw section 222 so that the pressing part may press the artificial anus protection plate 10 inside the cutting part 210.

Figure 11A:
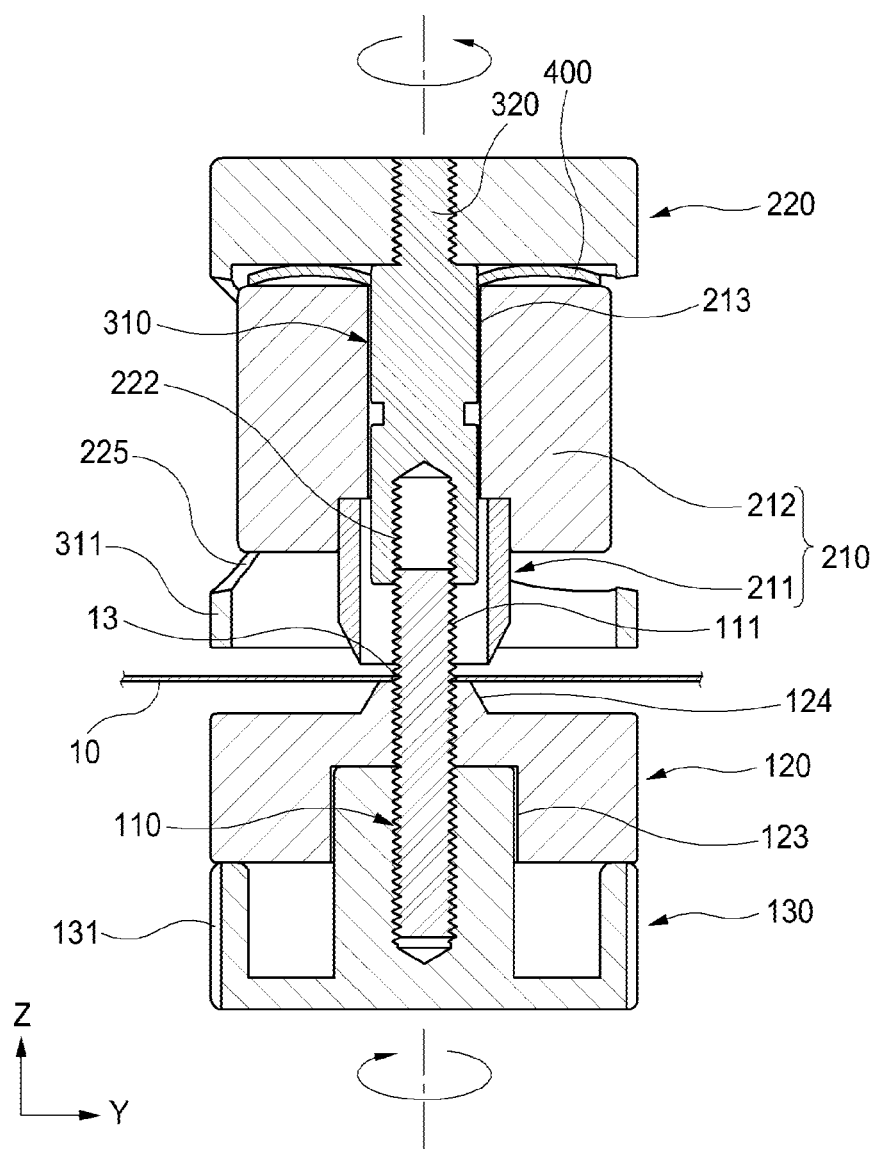
FIGS. 11A and 11B are cross-sectional views illustrating use examples of the device for cutting an artificial anus protection plate of FIG. 9.
Figure 11B:
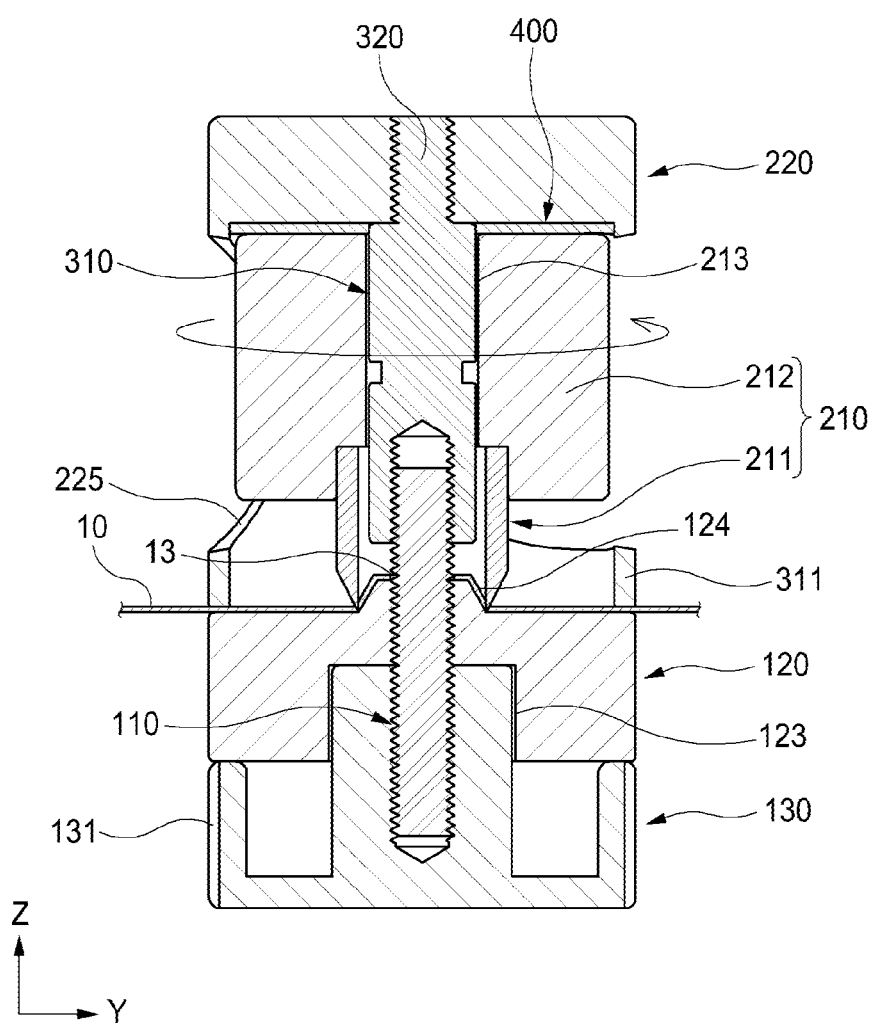
Figure 12:
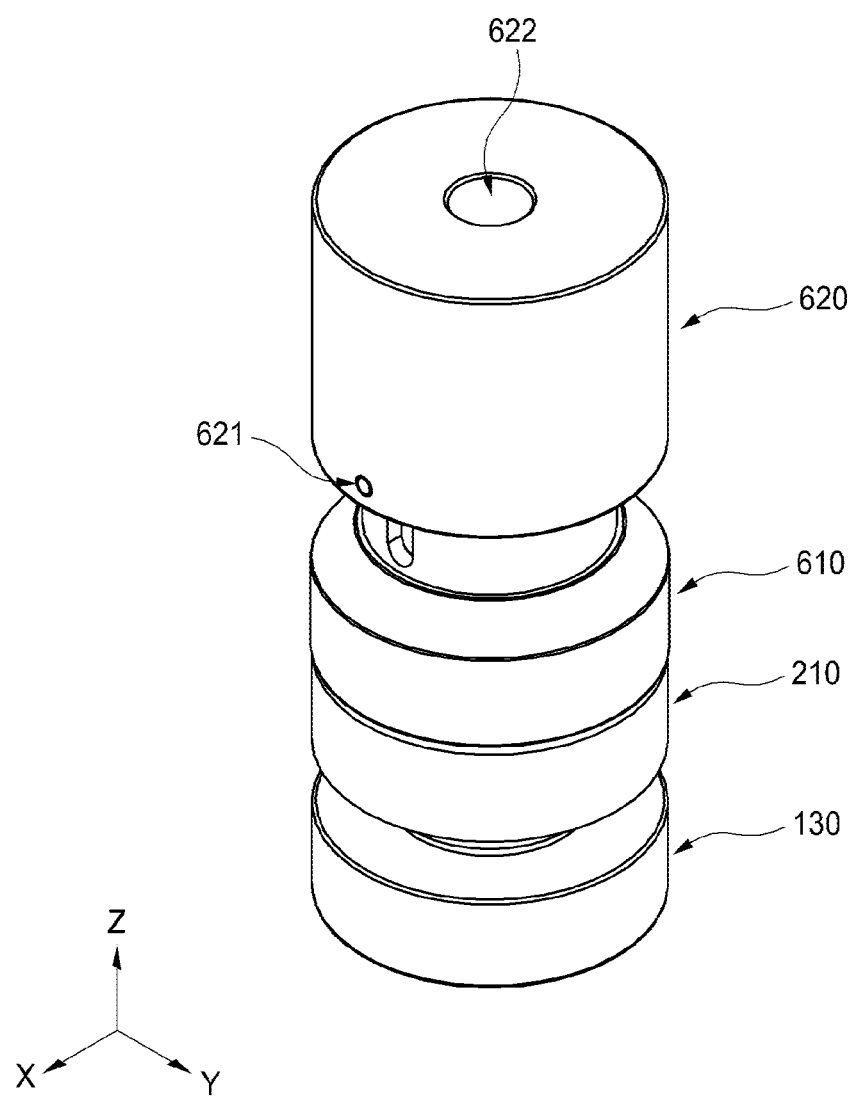
FIG. 12 is a perspective view illustrating a device for cutting an artificial anus protection plate in accordance with a third embodiment of the present invention.

In another example, as illustrated in FIGS. 11A and 11B, the pressing part 311 may protrude in the longitudinal direction from the pressing body 220 so that the pressing part may press the artificial anus protection plate 10 outside the cutting part 210.

Specifically, the pressing part 311 may protrude in the longitudinal direction from the pressing body 220 so that the cutting part 210 is located inside the pressing part.

At this point, the pressing part 311 is preferably provided with one or more openings 225 so that the cutting part 210 is exposed to the outside and a user may rotate the cutting part 210.

The openings 225 may have various shapes as long as the shapes are formed so that the user easily rotates the cutting part 210.

Through the above-mentioned configuration of the pressing part 311, the pressing body 220 presses the artificial anus protection plate 10 from the outside of the cutting part 210 and fix the artificial anus protection plate 10 to the support part, and then, the cutting part 210 may bore a hole in the artificial anus protection plate 10 by means of rotation.

Meanwhile, an elastic member 400 may be installed between the cutting part 210 and the pressing body 220 so that the cutting part 210 is pressed toward the support part 120.

The elastic member 400 is a component installed so that the cutting part 210 uniformly presses the artificial anus support plate 10 and forms a through hole, and may be variously configured.

For example, the elastic member 400 may be a plate spring installed between the inside of the pressing body 220 and the upper surface of the cutting part 210.

As illustrated in FIGS. 12 to 16B, a device for cutting an artificial anus protection plate in accordance with the present invention, includes: a protection plate support part 130 having a support surface 135 on which a coupling rod 110 passing through an artificial anus protection plate 10 is installed and which supports the artificial anus protection plate 10; a guide rod 500 screw-coupled to the coupling rod 110 in the lengthwise direction of the coupling rod 110; a cutting part 210 having a blade section 212 which is installed so as to be movable in the vertical direction with respect to the guide rod 500 and cuts the artificial anus protection plate 10 at a preset diameter; and a pressing means which is coupled to the guide rod 500 and presses and moves the cutting part 210 downward so that the blade section 212 cuts the artificial anus protection plate 10.

The artificial anus protection plate 10 is a component attached to the skin of a user so as to be couplable to a bowel bag 20, and may be variously configured.

For example, as illustrated in FIGS. 1A and 1B, the artificial anus protection plate 10 may include: a fixture 11 in which an opening section is detachably formed; and an attachment part 12 which is formed so that the bowel bag 20-attached fixture 11 may be tightly attached to the skin of a user.

At this point, in the central portion of the artificial anus protection plate 10, a cutting hole 13 may be formed so that the user may easily bore a hole at a position to cut.

Meanwhile, the device for cutting an artificial anus protection plate is characterized in that a through hole or the like is formed in the artificial anus protection plate 10 to fit the size of the stoma of the user with respect to the cutting hole 13, and characterized by including a protection plate support part 130 and a pressing means.

Here, an embodiment of the device for cutting an artificial anus protection plate in accordance with the present invention has been described in which a through hole is formed in the artificial anus protection plate 10. However, various cutting function may be performed by changing the shape and size of a blade according to uses thereof, for example, cutting or boring only a portion.

The protection plate support part 130 is a component in which the coupling rod 110 passing through the artificial anus protection plate 10 is installed and a support surface 135 for supporting the artificial anus protection plate 10 is formed, and may be variously configured.

Specifically, the protection plate support part 130 is a component which supports the artificial anus protection plate 10 so that the artificial anus protection plate 10 is cut when pressed by a pressing means to be described later, and may be variously configured.

For example, the protection plate support part 130 may have: a coupling rod 110 installed on an upper surface thereof and passing through the artificial anus protection plate 10; and a support surface 135 for supporting the artificial anus protection plate 10, and may have a cylindrical shape, such as a circular cylinder and a polygonal cylinder, so that a user may hold the protection plate support part by the hand when operating the pressing means to be described later.

In addition, on the outer peripheral surface of the protection plate support part 130, a sliding prevention means for preventing the sliding of the protection plate support part from the hand of a user during rotation may further be provided.

For example, the sliding prevention means may be formed by a plurality of protruding ribs formed on the outer peripheral surface of the handle part in the circumferential direction.

The plurality of ribs are components formed to allow a user to easily hold the ribs by the hand, and may have various shapes as long as the shapes are formed to be held by the hand of a user.

The support surface 135 is a portion which supports the artificial anus protection plate 10 so that the blade section 212 of the cutting part 210 to be described later is pressed and cuts, for example, bores a hole in, the artificial anus protection plate 10, and may be formed in a flat surface.

The coupling rod 110 is a component which has the male screw section 111 on the outer peripheral surface thereof so that the coupling rod 110 is inserted into the artificial anus protection plate 10 and then may be screw-coupled to the female screw section 510 of a guide rod 500 to be described later. The coupling rod may be variously coupled.

At this point, the male screw section 111 is preferably formed on at least a portion of the outer peripheral surface of the coupling rod 110 while being spaced apart from the upper end of the coupling rod.

As described above, when the male screw section 111 is formed on at least a portion of the outer peripheral surface of the coupling rod 110 while being spaced apart from the upper end of the coupling rod 110, a portion of the upper end portion on which the male screw section 111 is not formed is inserted and is then screw-coupled to the female screw section 510 of the guide rod 500. Thus, the moving distance of the guide rod 500 in the lengthwise direction of the coupling rod 110 is reduced, and the cutting time of the artificial anus protection plate 10 can thereby be reduced.

The male screw section 111 may have any structure as long as the structure can be screw-coupled to the female screw section 510 of the guide rod 500 to be described later.

The guide rod 500 is a component which is screw-coupled to the coupling rod 110 in the lengthwise direction of the coupling rod 110 and is installed to guide some components in the pressing means to be described later, and may be variously configured.

Figure 13:
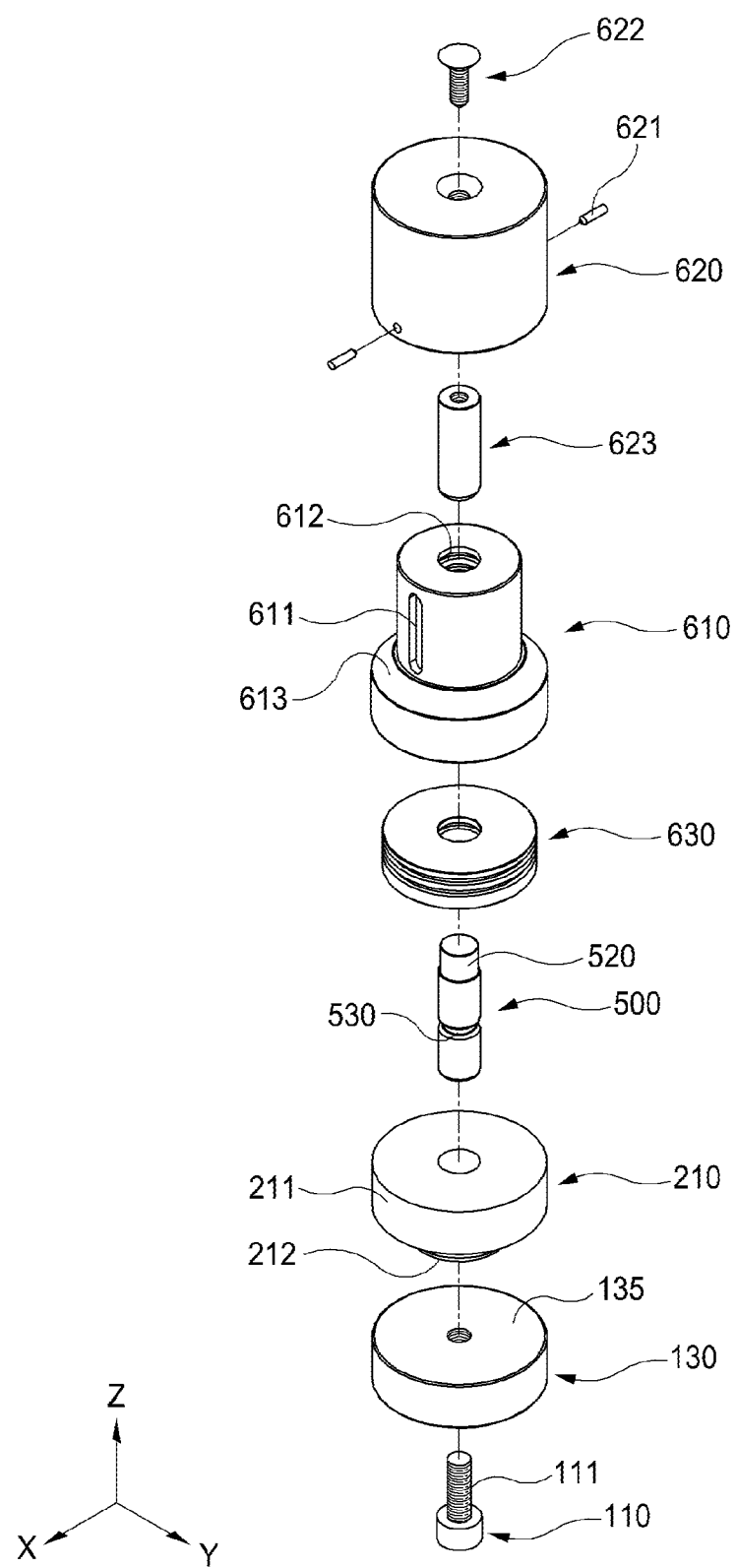
FIG. 13 is an exploded perspective view illustrating a configuration of the device for cutting an artificial anus protection plate of FIG. 12.

For example, as illustrated in FIG. 13, the guide rod 500 has a rod shape formed in the lengthwise direction of the coupling rod 110 and may have a female screw section 510 on an inner surface thereof so as to be screw-coupled to the coupling rod 110.

The cutting part 210 is a component which is installed so as to be movable in the vertical direction with respect to the guide rod 500 and is installed to cut the artificial anus protection plate 10, and may be variously configured.

For example, the cutting part 210 may be a blade which is formed in a circular shape to bore a hole in the artificial anus protection plate 10 at a preset diameter.

Specifically, the cutting part 210 is installed so as to be movable in the vertical direction with respect to the guide rod 500, and may have a blade section 212 for cutting the artificial anus protection plate 10 at a preset diameter.

For example, the cutting part 210 may include: a blade section 212 formed of a metal material; and a blade coupling part 211 to which the blade section 212 is fixedly installed.

More specifically, the cutting part 210 may have a structure in which the blade section 212 formed of a metal material is fixedly installed on the blade coupling part 211, the inside of which is formed of a synthetic resin material.

Here, the lower end of the blade section 212 may have any one shape among rectangles, circles, ellipses, polygons, and freely curved shapes. The blade coupling part 211 may have various structures according to the shape of the blade section 212.

Meanwhile, the cutting part 210 may have a sealing member 631 such as an O-ring on at least one among the inner peripheral surface thereof and the outer peripheral surface of the guide rod 500 so that the guide rod 500 is inserted in the lengthwise direction and retains a coupled state.

The sealing member 631 is a component in which the guide rod 500 is inserted in the lengthwise direction thereof without imparting substantial resistance to the vertical movement of the cutting part 210 and retains a coupled state, and may be formed of various materials.

Specifically, the sealing member 631 may be inserted into an insertion groove 530 formed in the outer peripheral surface of the guide rod 500 and coupled to the guide rod.

The pressing means is a component for pressing the cutting part 210 downward so that the blade section 212 cuts the artificial anus protection plate 10, and may be variously configured.

In addition, in order that the pressing means presses the cutting part 210, various methods such as pneumatic or hydraulic methods other than a mechanical method may also be used.

For example, the pressing means, as illustrated in FIGS. 12 to 14B and FIGS. 16A and 16B, may include a pressing part 630, a cylinder part 610, and a pressing body part 620.

Here, the pressing part 630, the cylinder part 610, and the pressing body part 620 are sequentially installed in the lengthwise direction of the guide rod 500.

The cylinder part 610 is a component in which the upper end of the guide rod 500 is inserted and coupled to the guide rod, and may be variously configured.

In particular, the cylinder part 610 is a component which is coupled to the pressing part 630 and the pressing body part 620 in order that the pressing part 630 presses the cutting part 210 according to the pressure change in a first cylinder space S1 and a second cylinder space S2, and may be variously configured according to the formation structure of the first cylinder space S1 and the second cylinder space S2.

The cylinder part 610 is formed in a pillar shape, and a through hole 619 is formed therein so that an upper end portion 520 of the guide rod 500 is inserted into and coupled to the through hole.

In addition, the through hole 619 is formed in the cylinder part 610 so that the guide rod 500 is inserted thereinto, and while the guide rod 500 is inserted, the upper portion of the guide rod may be used as the first cylinder space S1 to be described later.

Meanwhile, the cylinder part 610 may form the first cylinder space S1 and the second cylinder space S2 with a piston member 623 to be described later and the guide rod 500, and as in the embodiment illustrated in FIGS. 14A and 14B, and in the embodiment illustrated in FIGS. 16A and 16B, the cylinder part may form the first cylinder space S1 and the second cylinder space S2 inside the cylinder part 610 by means of various structures together with the guide rod 500 and the piston member 623 to be described later.

Figure 16A:
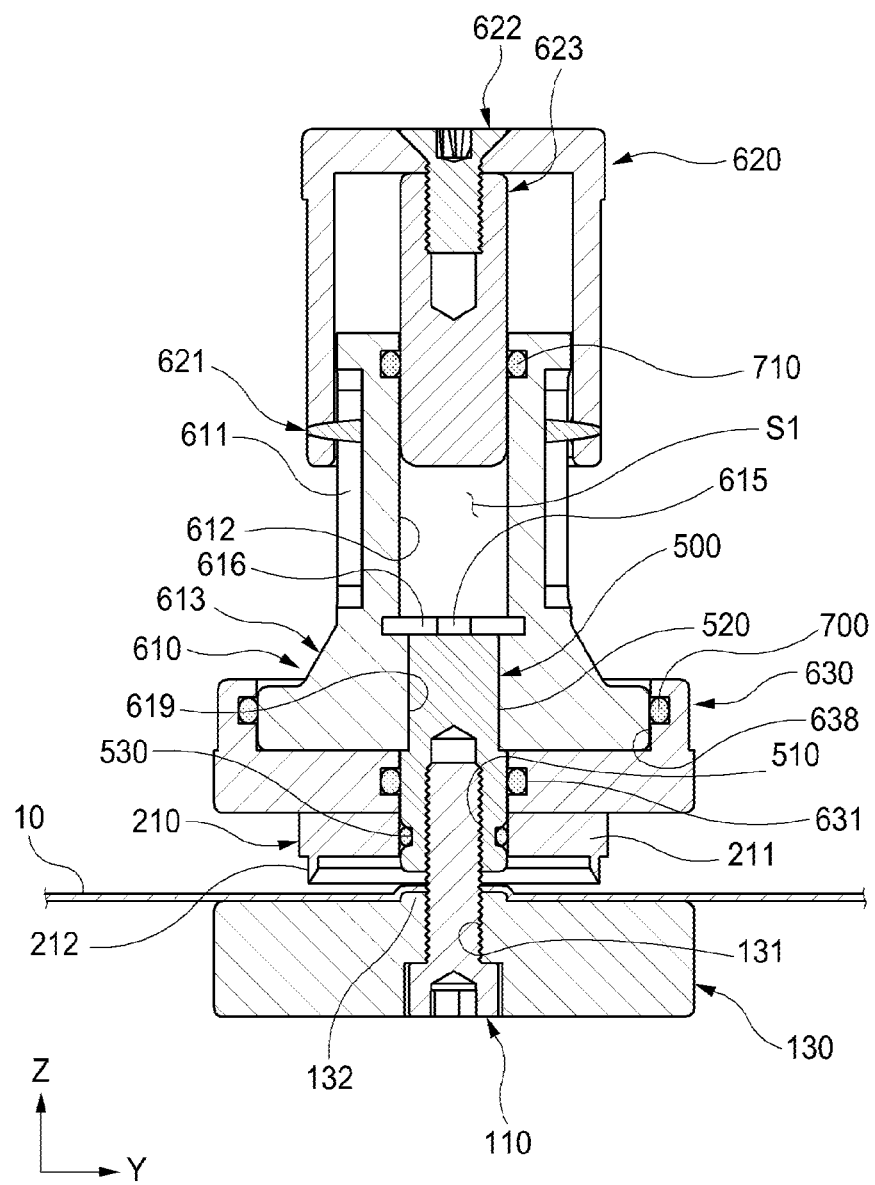
FIGS. 16A and 16B are cross-sectional views illustrating devices for cutting an artificial anus protection plate and illustrating the operation steps thereof in accordance a fourth embodiment of the present invention.
Figure 16B:
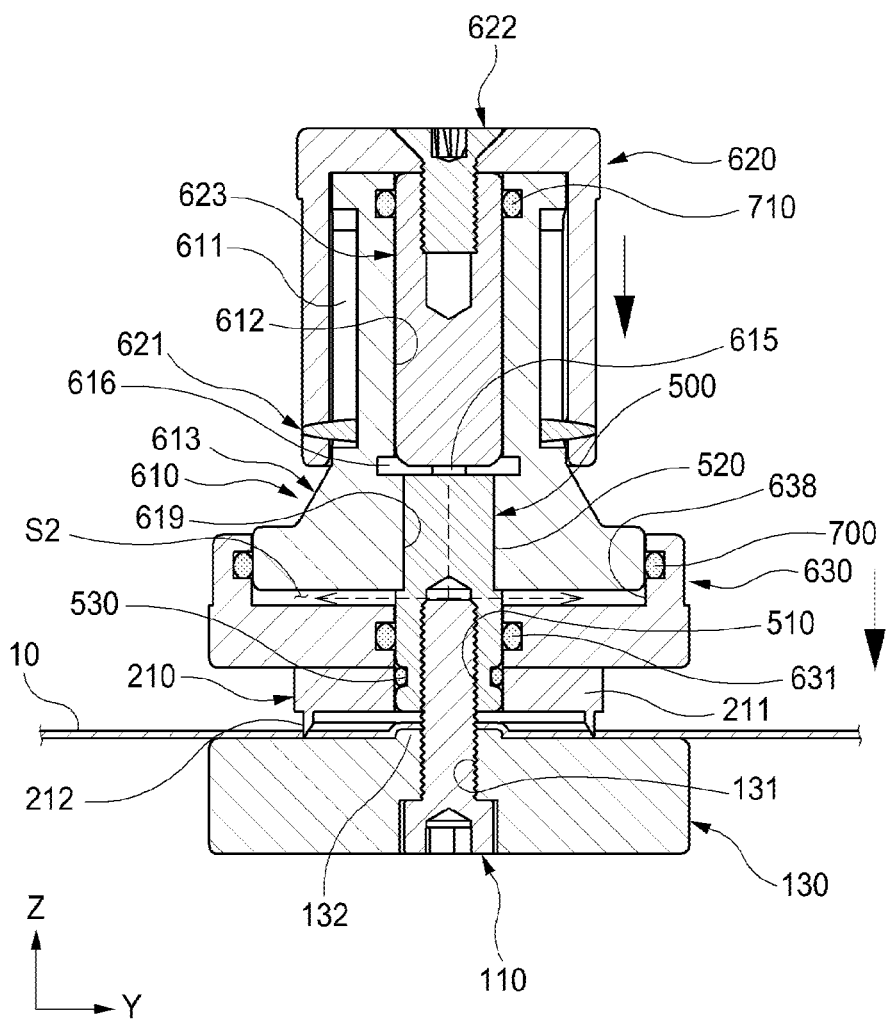

In addition, the cylinder part 610 may have a pillar shape as a whole, but according to a plan and a design, may have various external structures as in the embodiment illustrated in FIGS. 16A and 16B.

Figure 14A:
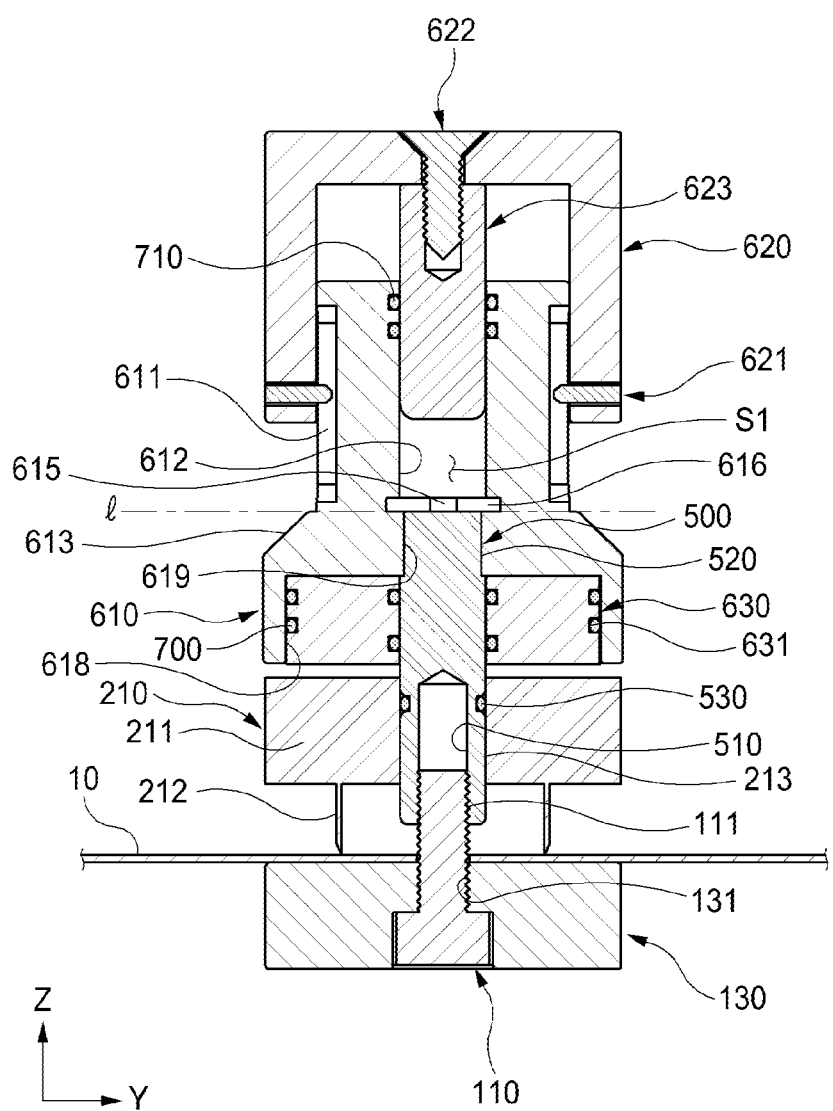
FIGS. 14A and 14B are cross-sectional views illustrating operation steps of the device for cutting an artificial anus protection plate of FIG. 12.
Figure 14B:
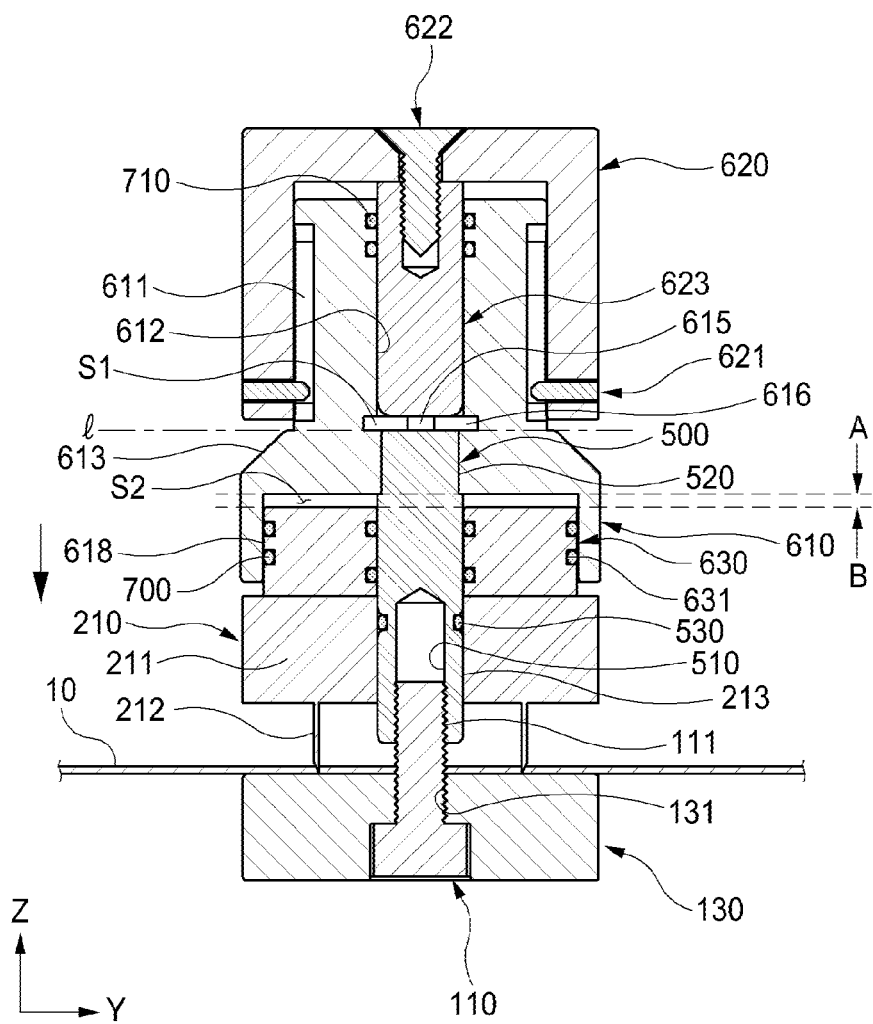

In a third embodiment, the cylinder part 610, as illustrated in FIGS. 14A and 14B, may be divided into an upper portion and a lower portion, the upper portion may be formed to have a relatively small outer diameter so as to be inserted into the pressing body part 620 to be described later, and the lower portion may be formed to have a larger diameter than the upper portion in order to be coupled to the pressing part 630 to be descried later.

Here, the outer diameter of the lower portion may have the same value as or a nearly approximate value to that of the pressing body part 620.

Meanwhile, the cylinder part 610 has a problem in that a portion of a finger is jammed in a boundary portion between the upper portion and the lower portion according to a vertical movement of the pressing body part 620, and to solve this problem, as illustrated in FIGS. 14A and 14B, a tapered section 613 in which the outer diameter thereof decreases toward the upper side thereof may be formed in the boundary portion between the upper portion and the lower portion.

In a second embodiment, the cylinder part 610, as illustrated in FIGS. 16A and 16B, may be divided into an upper portion and a lower portion, the upper portion may be formed to have a relatively small outer diameter so as to be inserted into the pressing body part 620 to be described later, and the lower portion may be formed to have a larger diameter than the upper portion to be coupled to the pressing part 630 to be descried later.

Here, the outer diameter of the lower portion may have the greater value than that of the pressing body part 620.

Meanwhile, the cylinder part 610 has a problem in that a portion of a finger is jammed in a boundary portion of the upper portion and the lower portion according to a vertical movement of the pressing body part 620, and to solve this problem, as illustrated in FIGS. 16A and 16B, a tapered section 613 in which the outer diameter thereof decreases toward the upper side thereof may be formed in the boundary portion between the upper portion and the lower portion.

The pressing part 630 is a component which is couple to the lower side of the cylinder part 610 so as to be movable in the vertical direction with respect to the cylinder part 610, forms a second cylinder space S2 with the cylinder part 610, and presses the cutting part 210 by means of the pressure in the second cylinder space S2. The pressing part may be variously configured.

The second cylinder space S2 is a space which communicates with the first cylinder space S1 to be described later through a communication flow passage 615 and presses the cutting part 210 by means of the pressure transferred from the first cylinder space S1, and may be variously formed according to the coupling structure of the cylinder part 610 and the pressing part 630.

In the third embodiment, the pressing part 630, as illustrated in FIGS. 14A and 14B, may include a cylinder member 610 which is installed to be vertically movable while being in close contact with an inner peripheral surface of a cylinder space section 618 formed on the bottom surface of the cylinder part 610.

More specifically, the cylinder space section 618 is concavely formed in a cylindrical shape on the bottom surface of the cylinder part 610, and the second cylinder space S2 is formed such that the cylinder member 610 is inserted into the cylinder space section 618.

In addition, the cylinder member 610 receives a pressure moving downward due to an increase in the pressure in the second cylinder space S2 and an increase in volume according to the increase in the pressure, and the pressure is transferred to the cutting part 210 installed under the cylindrical member, so that the cutting part 210 cuts the artificial anus protection plate 10.

Meanwhile, on at least one among the inner peripheral surface of the cylinder space section 618 and the outer peripheral surface of the cylinder member 610, a sealing member 700 such as an O-ring may be installed to seal the second cylinder space S2.

In addition, the cylinder member 610 may have a guide rod 500 installed to pass therethrough and a sealing member 631 such as an O-ring installed on at least one among the inner peripheral surface thereof and the outer peripheral surface of the guide rod 500.

In a fourth embodiment, the pressing part 630, as illustrated in FIGS. 16A and 16B, may include a cylinder member 610 having a cylinder space section 638 is formed on an upper side thereof so that the outer peripheral surface of the cylinder part 610 is inserted and is vertically movable therein.

More specifically, the cylinder space section 638 is concavely formed in a cylindrical shape on an upper surface of the pressing part 630, and the second cylinder space S2 is formed such that the cylinder member 610 is inserted into the cylinder space section 638.

In addition, the cylinder member 610 receives a pressure moving downward due to an increase in the pressure in the second cylinder space S2 and an increase in volume according to the increase in the pressure, and the pressure is transferred to the cutting part 210 installed under the cylindrical member, so that the cutting part 210 cuts the artificial anus protection plate 10.

Meanwhile, on at least one among the inner peripheral surface of the cylinder space section 638 and the outer peripheral surface of the cylinder part 610, a sealing member 700 such as an O-ring may be installed to seal the second cylinder space S2.

In addition, a guide rod 500 may be installed to pass therethrough the cylinder member 610 and a sealing member 631 such as an O-ring may be installed on at least one among the inner peripheral surface of the cylinder member and the outer peripheral surface of the guide rod 500.

Meanwhile, the pressing part 630 may have various coupling structures, for example, may be formed in a separate member from or integrally formed with the cutting part 210.

The pressing body part 620 is a component which is coupled to an upper side of the cylinder part 610 so as to be vertically movable with respect to the cylinder part 610, forms the first cylinder space S1 communicating with the second cylinder space S2 together with the cylinder part 610, and includes a piston member 623 moving downward along the first cylinder space S1 to allow the pressure in the first cylinder space S1 to be transferred to the second cylinder space S2. The pressing body part may be variously configured.

The first cylinder space S1 is a space which has a volume changing according to the vertical movement of the piston member 623 and allows the pressure in the first cylinder space S1 to be transferred to the second cylinder space S2 through a communication flow passage 615, and may be variously configured according to coupling structures of the pressing body part 620 and the cylinder part 610.

Here, the first cylinder space S1 may be formed in a cylindrical space by means of a cylinder formation hole 612 which is formed by extending a through hole 619 from the cylinder part 610 to an upper end of the cylinder part so that a volume change may be obtained by vertical movement of the piston member 623.

In addition, the first cylinder space S1 preferably has a smaller horizontal cross-sectional area than the second cylinder space S2 described above.

When the horizontal cross-sectional area of the first cylinder space S1 is smaller than the second cylinder space S2, a greater pressure may be applied to the pressing part 210 by means of a relatively small force.

The piston member 623 is a component which is inserted into the cylinder formation hole 612 formed in the cylinder part 610 so as to be vertically movable, and may be coupled to the pressing body part 620 as an integral member, or the piston member 623 may be coupled to the pressing body part 620 as a separate member by coupling member 622.

In addition, a sealing member 710 such as an O-ring may be installed to seal the first cylinder space S1 on at least one among the outer peripheral surface of the piston member 623 and the inner peripheral surface of the cylinder formation hole 612.

Meanwhile, the first cylinder space S1 communicates with the second cylinder space S2 through the communication flow passage 615 and may be variously connected according to the structure of the communication flow passage 615.

The communication flow passage 615 is a component for communication between the first cylinder space S1 and the second cylinder space S2, and may be formed in the lengthwise direction in at least one among the outer peripheral surface of the guide rod 500 and the inner peripheral surface of the cylinder member 610.

Figure 15A:
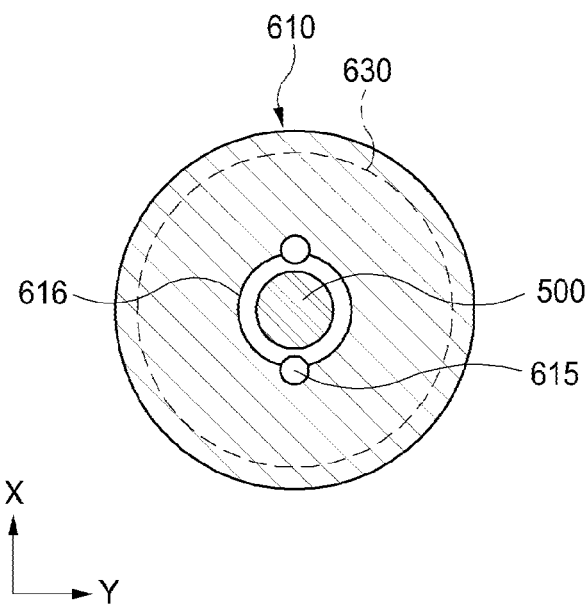
FIG. 15A is a cross-sectional view illustrating, in direction A, an inside of a cylinder part of a device for cutting an artificial anus protection plate in accordance with the present invention.
Figure 15B:
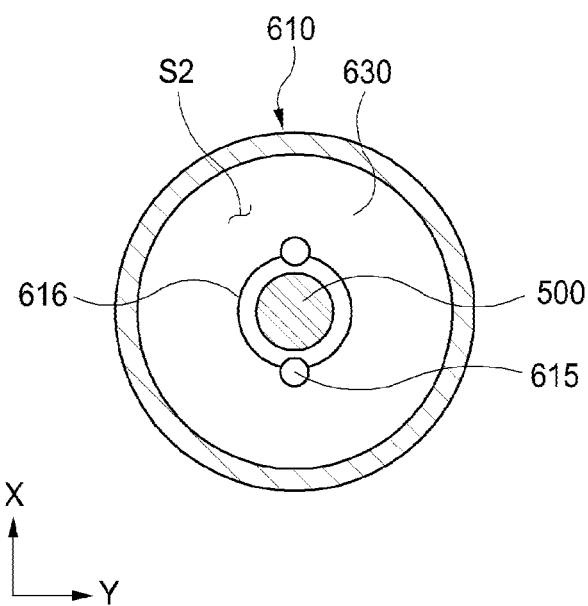
FIG. 15B is a cross-sectional view illustrating, in direction B, an inside of a cylinder part of a device for cutting an artificial anus protection plate in accordance with the present invention.

Specifically, the communication flow passage 615, as illustrated in FIGS. 15A and 15B, may be formed as a groove in the inner peripheral surface of the cylinder member 610 on the further outer side than the outer diameter of the through hole 618 in which the guide rod 500 is inserted.

In addition, at this point, on a lower end of the cylinder formation hole 612 of the cylinder member 610, an expansion section 616 having an expanded inner diameter for connection with the communication flow passage 615 may be formed.

Meanwhile, in the first cylinder space S1 and the second cylinder space S2, air, a fluid, etc. may be filled, and in order to apply a greater pressure, a fluid having a low compressibility is preferably filled.

The pressing body part 620 is formed so that an upper portion of the above-described cylinder member 610, that is, the upper portion with respect to line f in FIGS. 14A, 14B, 16A, and 16B is inserted thereinto, and may be installed to be vertically movable with respect the cylinder member 610 for a vertical movement of the piston member 623.

Preferably, the pressing body part 620 is prevented from rotating with respect to the cylinder member 610 when the protection plate support part 130 described above is screw-coupled in a sequentially coupled structure of the cylinder member 610 and the guide rod 500.

To this end, the pressing body part 620 may have a rotation prevention means installed therein to prevent rotation about the guide rod 500 as a rotation axis.

The rotation prevention means may include: one or more rotation prevention grooves 611 formed in the outer peripheral surface of the cylinder part 610 in the vertical direction; and engagement protrusions 621 protruding toward the inner peripheral surface of the pressing body part 620 and inserted into the rotation prevention grooves 611.

The rotation prevention grooves 611 are lengthily formed in the vertical direction so that the pressing body part 620 vertically moves with respect to the cylinder part 610.

The engagement protrusions 621 are components which protrude toward the inner peripheral surface of the pressing body part 620 and are inserted into the rotation prevention grooves 611. The engagement protrusions may be variously configured.

Meanwhile, the device for cutting artificial anus protection plate is used as follows.

Firstly, while the protection plate support part 130 is separated from the other components, as illustrated in FIG. 14A or 16A, the coupling rod 110 is inserted into the artificial anus protection plate 10.

After the coupling rod 110 is inserted into the artificial anus protection plate 10, the protection plate support part 130 is screw-coupled to the guide rod 500 described above.

At this point, when the coupling rod 110 and the guide rod 500 are screw-coupled, rotation of the pressing body part 620 with respect to the cylinder part 610 and the guide rod 500 is prevented, and thus, the coupling rod 110 and the guide 500 are smoothly coupled.

After the coupling rod 110 and the guide rod 500 are coupled, the pressing body part 620 is pressed downward while holding the protection plate support part 130 or supporting the protection plate support part against a table etc.

When the pressing body part 620 is pressed downward, the piston member 623 coupled to the pressing body part 620 is moved downward, and when the piston member 623 is moved downward, the volume of the first cylinder space S1 is reduced.

When the volume of the first cylinder space S1 is reduced, the fluid in the first cylinder space S1 is moved to the second cylinder space S2 through the communication flow passage 615.

When the fluid in the second cylinder space S2 increases, the volume of the fluid increases. Therefore, the pressing part 630 coupled to form the second cylinder space S2 is moved downward by means of hydraulic pressure, and presses down the cutting part 210 located thereunder.

Accordingly, the cutting part 210 is moved downward along the lengthwise direction of the guide rod 500 by means of pressing of the pressing part 630, and the blade section 212 cuts, for example, bores a hole in, the artificial anus protection plate 10 supported on the support surface 135 of the protection plate support part 130.

Meanwhile, the artificial anus protection plate 10 is cut through various methods such as boring or cutting according to various sizes, shapes, etc. thereof. To this end, according to each of cutting conditions, the cutting part 210 may be replaced, from the guide rod 500, with a cutting part 210 provided with a blade section 212 having the corresponding shape and size.

As described so far, a user may conveniently cut, for example, bore a hole in the artificial anus protection plate 10 by using a device for cutting an artificial anus protection plate in accordance with the present invention.

The above-disclosed subject matter merely describes some portions of preferred embodiments that can be implemented by the present invention. Therefore, as is well known, the scope of the invention shall not be construed as limited to the embodiments above, and technical ideas that share a base with the aforementioned technical idea of the present invention would all be included in the scope of the invention.

The invention claimed is:

1. A device for cutting an artificial anus protection plate, the device comprising:
   a protection plate support part in which a coupling rod passing through an artificial anus protection plate is installed and a support surface for supporting the artificial anus protection plate is formed;
   a guide rod screw-coupled to the coupling rod in a lengthwise direction of the coupling rod;
   a cutting part installed so as to be movable in a vertical direction with respect to the guide rod and having a blade section for cutting the artificial anus protection plate at a preset diameter; and
   a pressing means which is coupled to the guide rod and presses to move the cutting part downward so that the blade section cuts the artificial anus protection plate;
   wherein the pressing means comprises:
   a cylinder part to which an upper end of the guide rod is inserted and coupled;
   a pressing part which is coupled to a lower side of the cylinder part so as to be movable in the vertical direction with respect to the cylinder part and forms a second cylinder space with the cylinder part and which presses the cutting part by means of a pressure inside the second cylinder space; and
   a pressing body part which is coupled to an upper side of the cylinder part so as to be movable in the vertical direction with respect to the cylinder part, forms a first cylinder space communicating with the second cylinder space together with the cylinder part, and comprises a piston member moving downward along the first cylinder space such that a pressure in the first cylinder space is transferred to the second cylinder space.

2. The device for cutting an artificial anus protection plate of claim 1, wherein the pressing part comprises a cylinder member which is installed so as to be movable in the vertical direction while being in close contact with an inner peripheral surface of the cylinder space section formed in a bottom surface of the cylinder part.

3. The device for cutting an artificial anus protection plate of claim 1, wherein the pressing part comprises a cylinder member in which a cylinder space section is formed in an upper portion thereof so that an outer peripheral surface of the cylinder part is inserted in the cylinder space section and is movable in the vertical direction.

4. The device for cutting an artificial anus protection plate of claim 1, wherein the pressing part is formed as a separate member from the cutting part or integrally formed with the cutting part.

5. The device for cutting an artificial anus protection plate of claim 1, wherein the pressing body part comprises a rotation prevention means installed therein to prevent rotation about the guide rod as a rotation axis; and
   wherein the rotation prevention means comprises:
   one or more rotation prevention grooves formed in the outer peripheral surface of the cylinder part in the vertical direction; and
   engagement protrusions protruding toward the inner peripheral surface of the pressing body part and inserted into the rotation prevention grooves.

6. The device for cutting an artificial anus protection plate of claim 1, wherein:
   the blade section is formed of a metal material; and
   the cutting part further comprises a blade coupling section to which the blade section is fixedly installed.

7. The device for cutting an artificial anus protection plate of claim 6, wherein a lower end of the blade section has circle shapes.

* * * * *